(12) United States Patent
Higashiyama

(10) Patent No.: US 12,285,568 B2
(45) Date of Patent: Apr. 29, 2025

(54) HUMIDIFICATION DEVICE AND RESPIRATORY HUMIDIFICATION AND BLOWING APPARATUS INCLUDING THE SAME

(71) Applicant: Murata Manufacturing Co., Ltd., Kyoto (JP)

(72) Inventor: Yuzo Higashiyama, Kyoto (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 1108 days.

(21) Appl. No.: 17/143,443

(22) Filed: Jan. 7, 2021

(65) Prior Publication Data
US 2021/0128866 A1 May 6, 2021

Related U.S. Application Data

(63) Continuation of application No. PCT/JP2019/024453, filed on Jun. 20, 2019.

(30) Foreign Application Priority Data

Aug. 22, 2018 (JP) .................................. 2018-155616

(51) Int. Cl.
*A61M 16/16* (2006.01)
*A61M 16/00* (2006.01)
*A61M 16/14* (2006.01)

(52) U.S. Cl.
CPC ...... *A61M 16/147* (2014.02); *A61M 16/0066* (2013.01); *A61M 16/024* (2017.08);
(Continued)

(58) Field of Classification Search
CPC ............ A61M 16/147; A61M 16/0066; A61M 16/024; A61M 16/145; A61M 16/16;
(Continued)

(56) References Cited

U.S. PATENT DOCUMENTS 4,366,105 A * 12/1982 Nowacki ............. A61M 16/109
261/DIG. 65
4,644,790 A * 2/1987 Mizoguchi .............. G01F 23/02
261/DIG. 65
(Continued)

FOREIGN PATENT DOCUMENTS

JP S59168859 A 9/1984
JP 2005058709 A 3/2005
(Continued)

OTHER PUBLICATIONS

International Search Report issued in Application No. PCT/JP2019/024453, dated Aug. 27, 2019.
(Continued)

*Primary Examiner* — Timothy A Stanis
*Assistant Examiner* — Tina Zhang
(74) *Attorney, Agent, or Firm* — McDonald Hopkins LLC

(57) ABSTRACT

A humidification device (200A) includes a reservoir (216), a vaporizer (250), a water supply passage (230), a gas introduction passage (240), a gas introduction source (260), and a controller. The reservoir (216) stores water. The vaporizer (250) vaporizes the water supplied to the vaporizer (250). The water supply passage (230) is connected to the reservoir (216) and the vaporizer (250) and filled with the water flowing from the reservoir (216). The gas introduction passage (240) is connected to an intermediate position of the water supply passage (230). The gas introduction source (260) introduces gas into the water supply passage (230) through the gas introduction passage (240) so as to push out, by using pressure of the introduced gas, toward the vaporizer (250) the water with which the water supply passage (230) is filled. The controller controls operation of the gas introduction source (260).

16 Claims, 18 Drawing Sheets

(52) U.S. Cl.
CPC .......... *A61M 16/145* (2014.02); *A61M 16/16* (2013.01); *A61M 2016/0018* (2013.01); *A61M 2016/0027* (2013.01); *A61M 2016/0033* (2013.01); *A61M 2205/0294* (2013.01)

(58) Field of Classification Search
CPC .. A61M 2016/0018; A61M 2016/0027; A61M 2016/0033; A61M 2205/0294; A61M 16/06; A61M 11/042; A61M 16/161; A61M 2016/0039; A61M 2205/3368; A61M 2205/42; A61M 2230/40; A61M 16/0883; A61M 16/1075–1095; A61M 15/06; A61M 2205/362; F24F 6/025; F04B 43/046
USPC ................. 128/203.16; 261/28, 65; 137/888; 417/65
See application file for complete search history.

(56) References Cited

U.S. PATENT DOCUMENTS

| | | | | |
|---|---|---|---|---|
| 4,942,874 A | * | 7/1990 | Terada | A61M 11/065 128/203.17 |
| 5,134,079 A | * | 7/1992 | Cusack | G01N 35/08 436/52 |
| 6,102,037 A | | 8/2000 | Koch | |
| 9,402,973 B2 | * | 8/2016 | Phillips | A61M 25/007 |
| 2009/0267242 A1 | * | 10/2009 | Nichols | A61M 11/007 261/151 |
| 2010/0065051 A1 | | 3/2010 | Potharaju et al. | |
| 2013/0263851 A1 | * | 10/2013 | Arcilla | A61M 16/1075 128/203.14 |
| 2015/0165146 A1 | * | 6/2015 | Bowman | A61M 16/161 128/203.14 |
| 2015/0322969 A1 | * | 11/2015 | Tanaka | E21B 43/121 417/55 |

FOREIGN PATENT DOCUMENTS

| | | |
|---|---|---|
| JP | 2005098630 A | 4/2005 |
| JP | 2014166495 A | 9/2014 |

OTHER PUBLICATIONS

Written Opinion issued in Application No. PCT/JP2019/024453, dated Aug. 27, 2019.

* cited by examiner

HUMIDIFICATION DEVICE AND RESPIRATORY HUMIDIFICATION AND BLOWING APPARATUS INCLUDING THE SAME

CROSS REFERENCE TO RELATED APPLICATION

This is a continuation of International Application No. PCT/JP2019/024453 filed on Jun. 20, 2019 which claims priority from Japanese Patent Application No. 2018-155616 filed on Aug. 22, 2018. The contents of these applications are incorporated herein by reference in their entireties.

BACKGROUND OF THE DISCLOSURE

Field of the Disclosure

The present disclosure relates to a humidification device that vaporizes water to humidify a humidification target gas and relates to a respiratory humidification and blowing apparatus that includes the humidification device.

Description of the Related Art

To date, various types of humidification mechanisms have been conceived, and, an optimum humidification mechanism is selected from among these and used in accordance with an application to which a product is applied. A respiratory humidification and blowing apparatus is one of the product groups to which the humidification mechanism is applied. Examples of the respiratory humidification and blowing apparatus include a continuous positive airway pressure (CPAP) device, a steam inhaler, an oxygen inhaler, and so forth.

Out of these, the CPAP device is used for treatment of the sleep apnea syndrome and feeds air to the airway of a sleeping user. More specifically, the CPAP device is configured such that the CPAP device that includes a blower therein continues to feed the air to a mask attached over the user's nose or mouth through a tube. In some cases, a humidification device is incorporated in the CPAP device. The CPAP device in which the humidification device is incorporated humidifies the air to be fed to the user.

Examples of the CPAP device in which the humidification device is incorporated include, for example, a device disclosed in Japanese Unexamined Patent Application Publication No. 2014-166495 (Patent Document 1). In the CPAP device disclosed in this document, a heater is installed on the lower side of a tank in which water is stored. When this heater is driven, the water stored in the tank is heated. A blowing passage is configured such that an air current generated by a blower passes through the upper side of the tank, thereby the air current contains water vapor generated by heating with the heater. In this way, the humidified air is fed to the airway of the user.

Patent Document 1: Japanese Unexamined Patent Application Publication No. 2014-166495

BRIEF SUMMARY OF THE DISCLOSURE

However, although the humidification device to be incorporated in the respiratory humidification and blowing apparatus represented by the above-described CPAP device is not required to generate a large amount of water vapor at a time, it is required for this humidification device to continuously generate a small amount of water vapor. Thus, from the viewpoints of energy efficiency, it cannot necessarily be said that the humidification device as disclosed in the above-described patent document is effective.

As the humidification device to be incorporated in the respiratory humidification and blowing apparatus, there are provided humidification devices having various configurations other than the above-described configuration. However, any of such humidification devices has complex configurations or include expensive components. Accordingly, it is difficult to say that these humidification devices are effective from the viewpoints of size reduction or the manufacturing cost. Furthermore, most of these humidification devices have low maintainability for, for example, cleaning inside the device, which is required to be kept clean.

Accordingly, the present disclosure is made in view of the above-described problems and aims to provide a humidification device that is small in size and can efficiently perform humidification and a respiratory humidification and blowing apparatus that includes this humidification device.

A humidification device according to a first aspect of the present disclosure includes a reservoir, a vaporizer, a water supply passage, a gas introduction passage, a gas introduction source, and a controller. The reservoir stores water. The vaporizer vaporizes the water supplied to the vaporizer. The water supply passage is connected to the reservoir at one end portion and the vaporizer at another end portion. The water supply passage is filled with the water flowing into the water supply passage when the water stored in the reservoir flows into the water supply passage through the one end portion. The gas introduction passage is connected to an intermediate position of the water supply passage. The gas introduction source introduces gas into the water supply passage through the gas introduction passage so as to push out, by using pressure of the introduced gas, toward the vaporizer the water with which a portion of the water supply passage between the intermediate position and the other end portion is filled, thereby supplying the water to the vaporizer. The controller controls operation of the gas introduction source. The controller drives the gas introduction source in an intermittent manner such that filling of the water supply passage with the water and introduction of the gas to the intermediate position are repeated alternately in terms of time.

In the humidification device according to the first aspect of the present disclosure, it is preferable that the gas introduction source include a piezoelectric pump.

In the humidification device according to the first aspect of the present disclosure, the gas introduction source may introduce air to the water supply passage.

In the humidification device according to the first aspect of the present disclosure, it is preferable that a penetration preventer that prevents penetration of the water from the water supply passage to the gas introduction source be provided in the gas introduction passage.

A humidification device according to a second aspect of the present disclosure includes a reservoir, a vaporizer, a water supply passage, a heating source, and a controller. The reservoir stores water. The vaporizer vaporizes the water supplied to the vaporizer. The water supply passage is connected to the reservoir at one end portion and the vaporizer at another end portion. The water supply passage is filled with the water flowing into the water supply passage when the water stored in the reservoir flows into the water supply passage through the one end portion. The heating source locally heats the water with which an intermediate position of the water supply passage is filled so as to generate water vapor, thereby pushing out, by using pressure of the generated water vapor, toward the vaporizer the water with which a portion of the water supply passage between the intermediate position and the other end portion is filled so as to supply the water to the vaporizer. The controller controls operation of the heating source. The controller drives the heating source in an intermittent manner such that filling of the water supply passage with the water and generation of the water vapor at the intermediate position are repeated alternately in terms of time.

In the humidification device according to the first and second aspects of the present disclosure, it is preferable that the water supply passage be filled with the water by utilizing capillarity or a water head difference.

In the humidification device according to the first and second aspects of the present disclosure, it is preferable that a check valve that allows movement of fluid from the water supply passage toward the vaporizer and that limits movement of the fluid from the vaporizer toward the water supply passage be provided at the other end portion.

In the humidification device according to the first and second aspects of the present disclosure, it is preferable that water repellent treatment be provided on one or both of a flow passage forming surface of the other end portion and an end surface of the other end portion.

In the humidification device according to the first and second aspects of the present disclosure, it is preferable that the vaporizer include a heater that heats the water supplied to the heater.

A respiratory humidification and blowing apparatus according to the present disclosure includes a blowing device that includes a blower for feeding gas to an airway of a user and the humidification device according to the first or second aspects of the present disclosure. In this respiratory humidification and blowing apparatus, a gas current generated by driving the blower is humidified by the humidification device.

The respiratory humidification and blowing apparatus according to the present disclosure may further include a respiratory state detector for detecting a respiratory state of the user. In this case, it is preferable that the controller determine whether the user performs inhaling operation or exhaling operation in accordance with a result of detection performed by the respiratory state detector. Also, in this case, it is preferable that, in the case where the controller determines that the user performs the inhaling operation, humidification operation with the humidification device be performed, and, in the case where the controller determines that the user performs the exhaling operation, the humidification operation with the humidification device be stopped.

In the respiratory humidification and blowing apparatus according to the present disclosure, it is preferable that the vaporizer be able to perform vaporization operation once or a plurality of times during a period of time after a time at which the controller determines that the user performs the inhaling operation to a time at which the controller determines that the user performs the exhaling operation.

According to the present disclosure, the humidification device can be made to be small in size and can efficiently perform humidification, and the respiratory humidification and blowing apparatus can include this humidification device.

Each of FIGS. 11A and 11B is a timing chart for description of humidification operation of the CPAP device according to the first embodiment.

Figure 12:
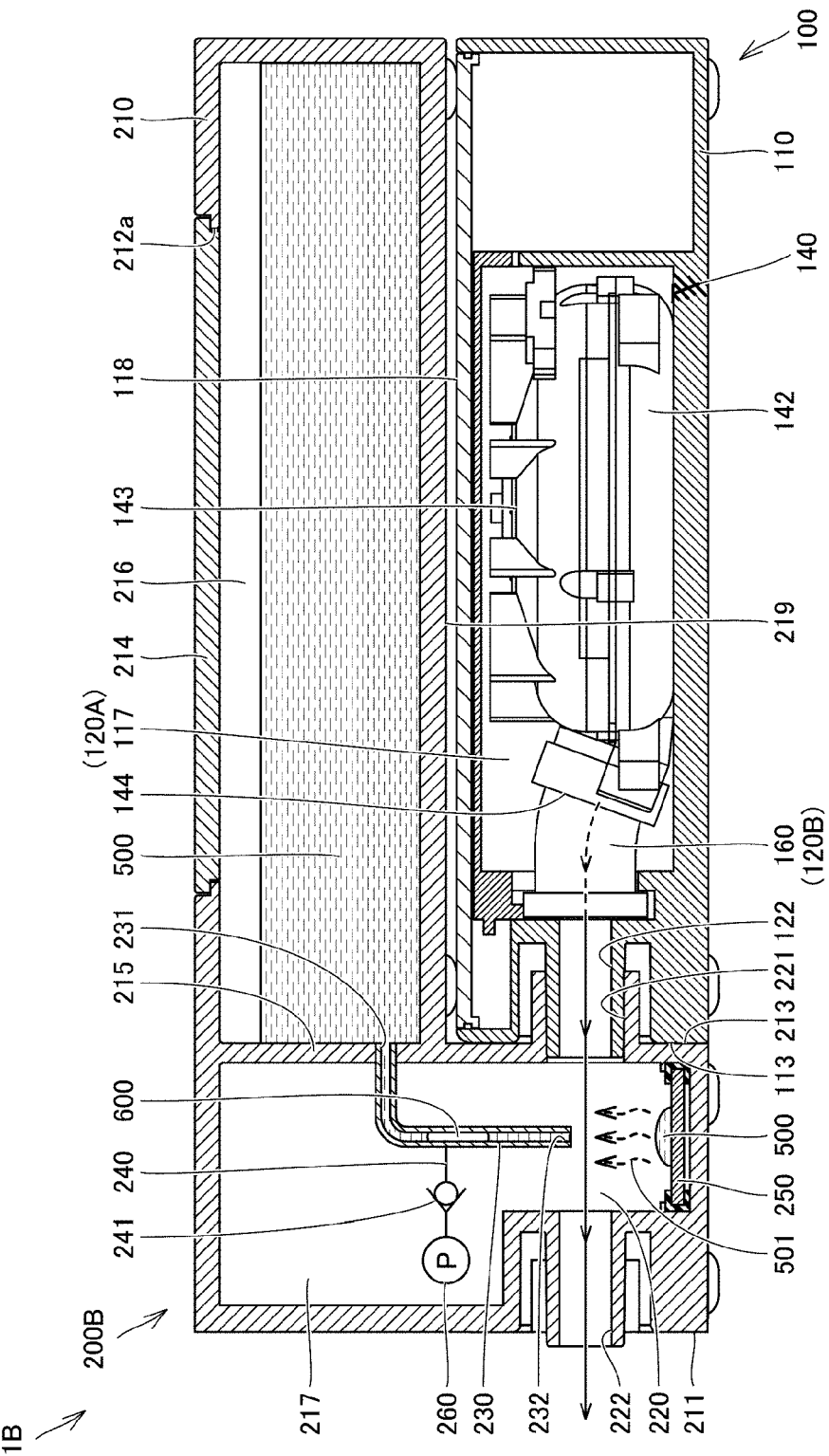

FIG. 12 is a schematic sectional view of a CPAP device according to a second embodiment in the first use state.

FIGS. 13A to 13D include schematic sectional views of specific examples of the structure of the water discharge port of the water supply passage illustrated in FIG. 12.

Figure 14:
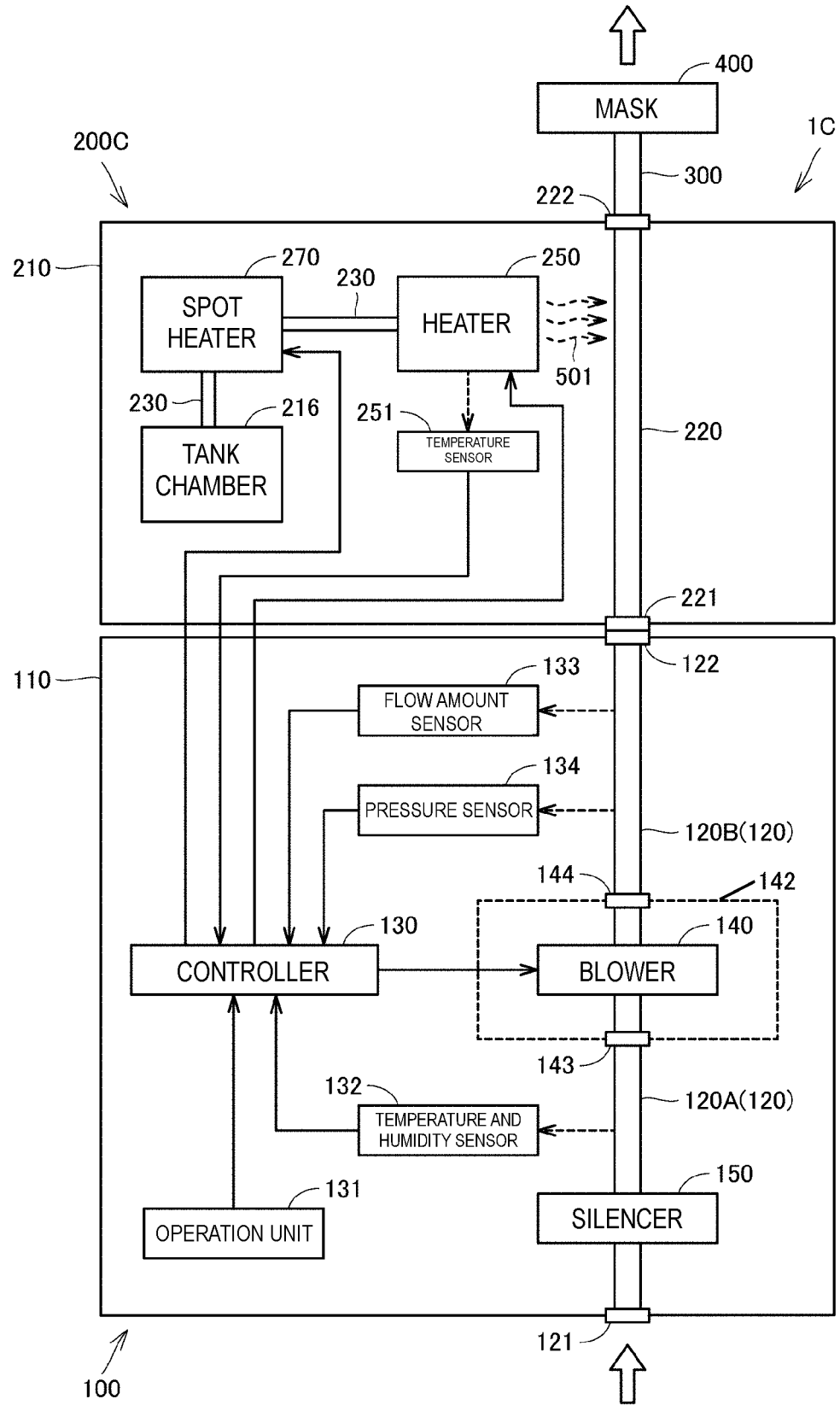

FIG. 14 illustrates the configuration of functional blocks of a CPAP device according to a third embodiment in the first use state.

Figure 15:
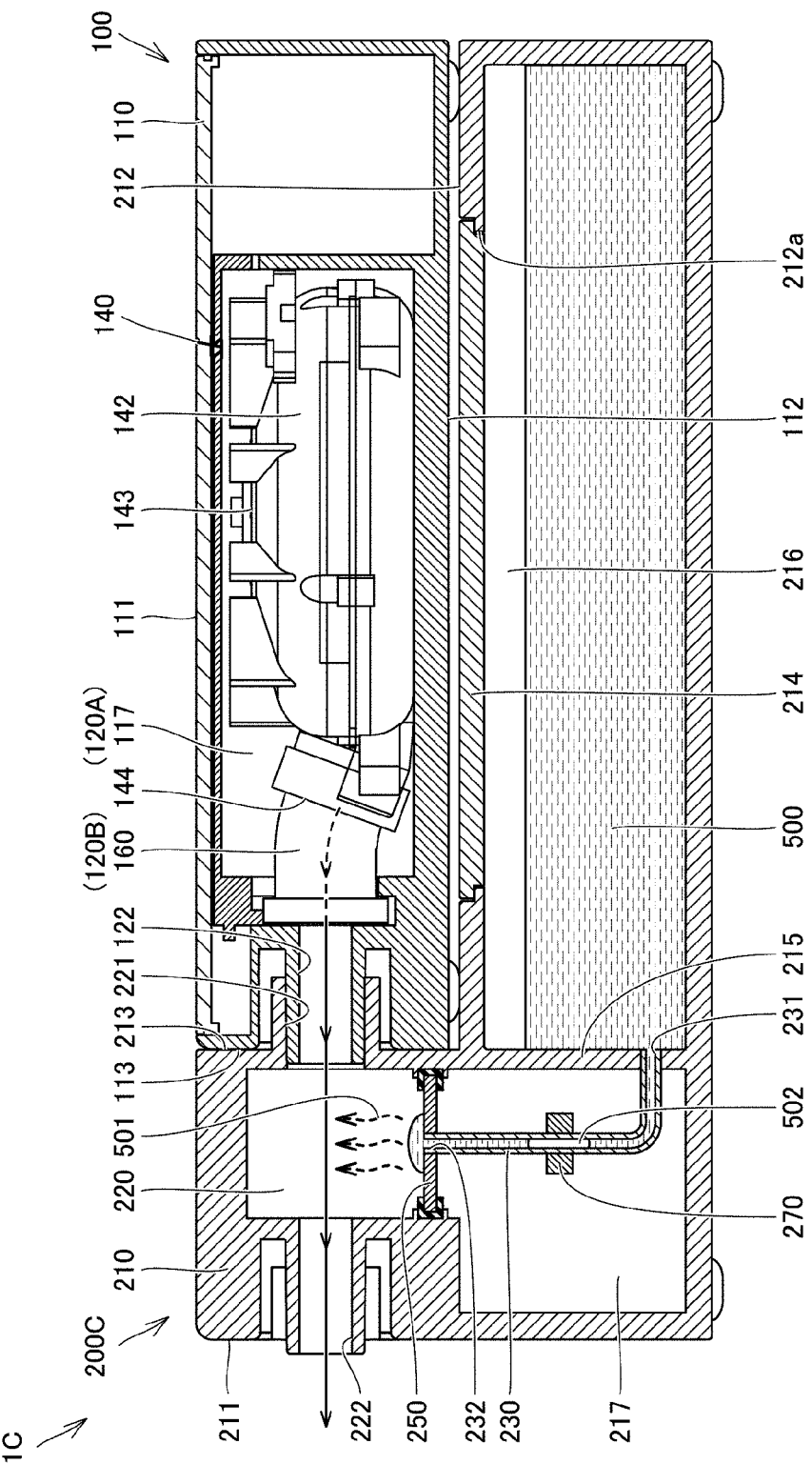

FIG. 15 is a schematic sectional view of the CPAP device according to the third embodiment in the first use state.

FIGS. 16A to 16D include schematic views for description of the vaporization operation in the CPAP device according to the third embodiment.

Figure 17:
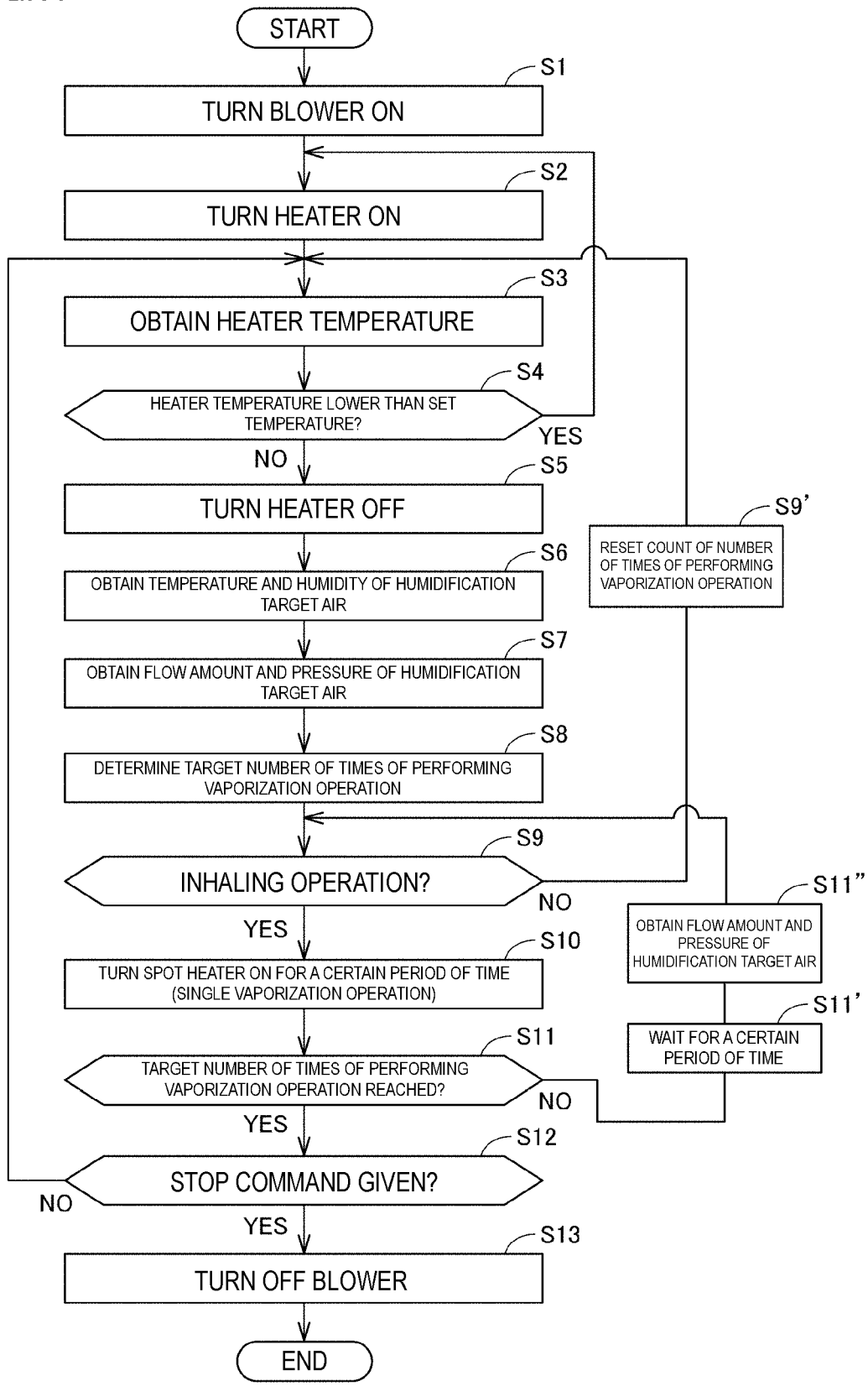

FIG. 17 is a flowchart illustrating the operation of the controller of the CPAP device according to the third embodiment in the first use state.

Figures 18A, 18B:
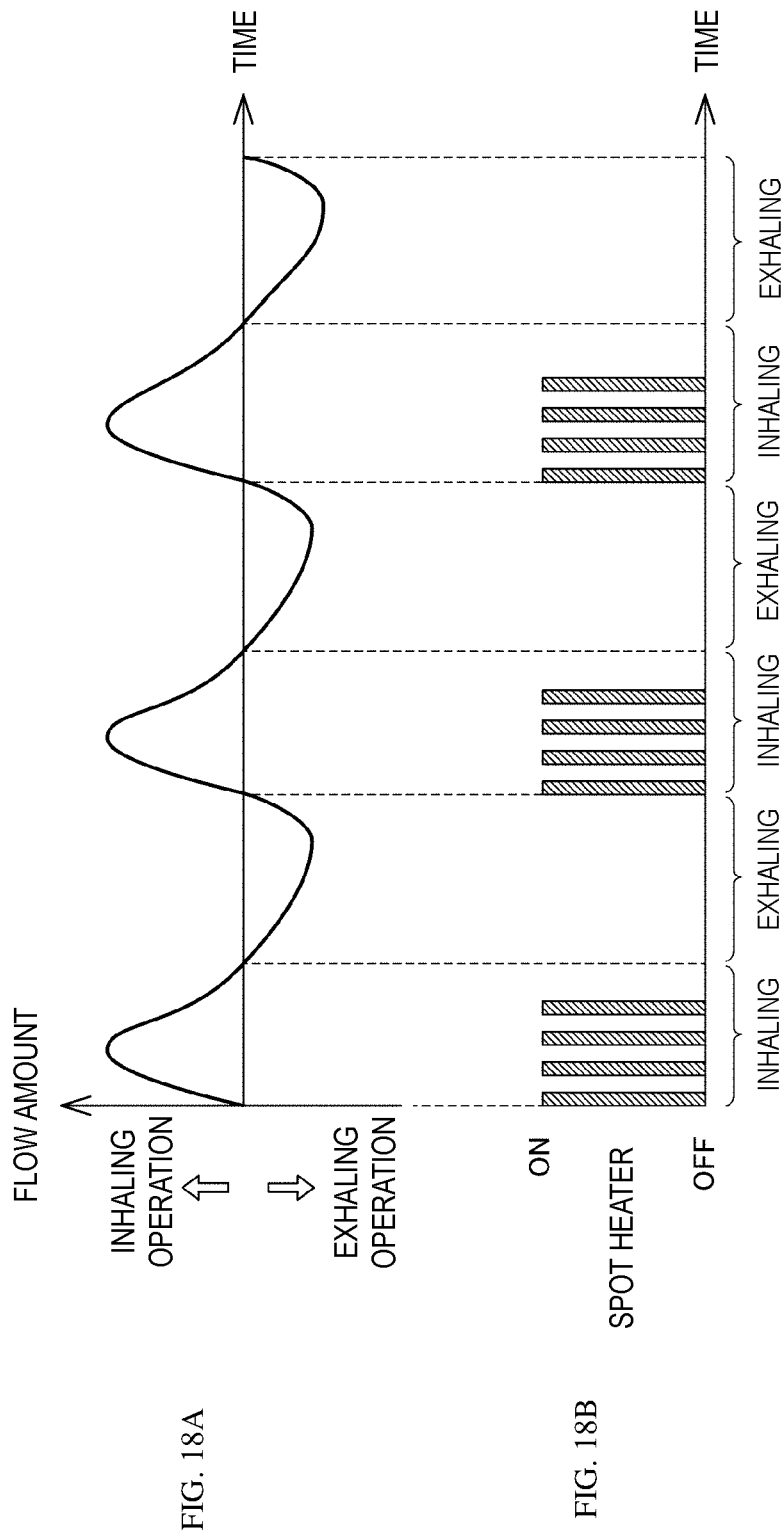

Each of FIGS. 18A and 18B is a timing chart for description of the humidification operation of the CPAP device according to the third embodiment.

DETAILED DESCRIPTION OF THE DISCLOSURE

Embodiments of the present disclosure will be described in detail below with reference to the drawings. The embodiments described below exemplify the cases where the present disclosure is applied to a respiratory humidification and blowing apparatus, a continuous positive airway pressure (CPAP) device that is, as a humidification device, incorporated in the respiratory humidification and blowing apparatus, and the humidification device incorporated in the CPAP device. In the embodiments described below, the same or common parts are denoted by the same reference signs in the drawings, and the description of the same or common parts is not repeated.

First Embodiment

Figure 1:
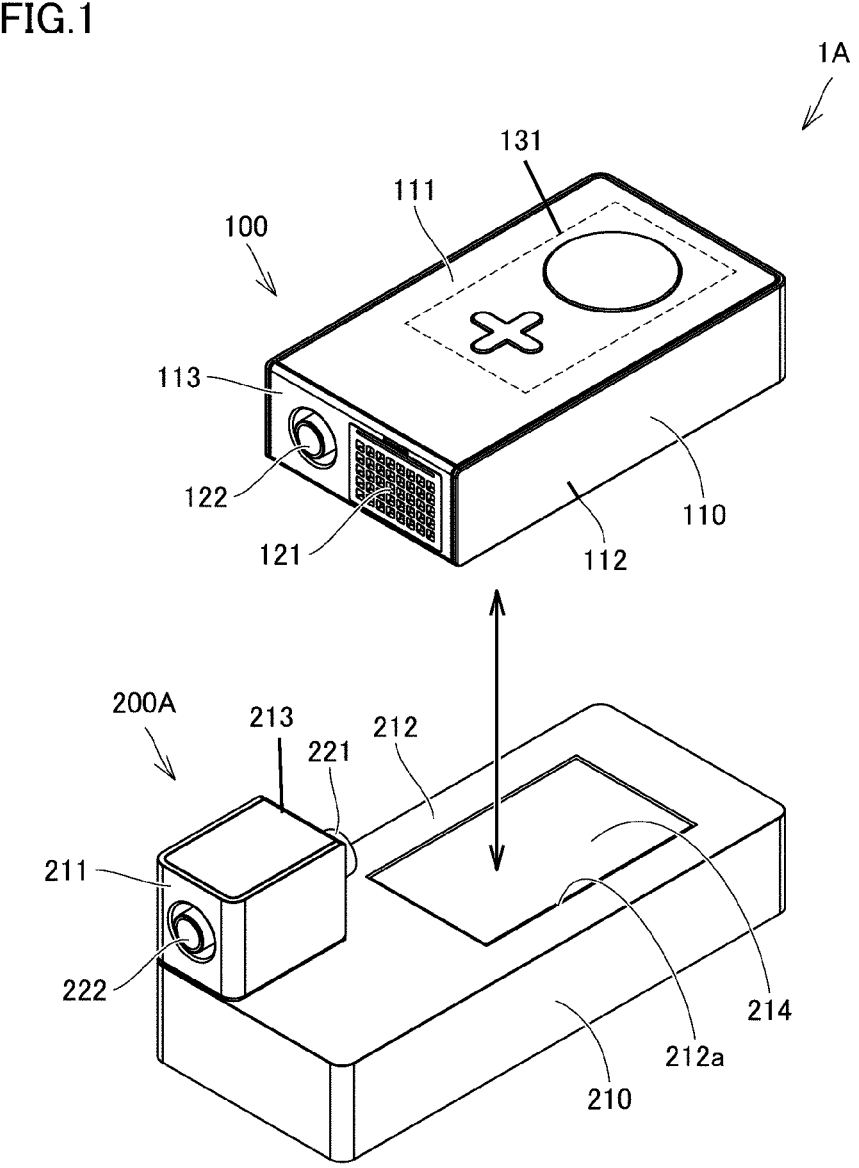
FIG. 1 is a perspective view illustrating an attachment/detachment manner of a blowing unit and a humidification unit of a continuous positive airway pressure (CPAP) device according to a first embodiment.
Figure 2:
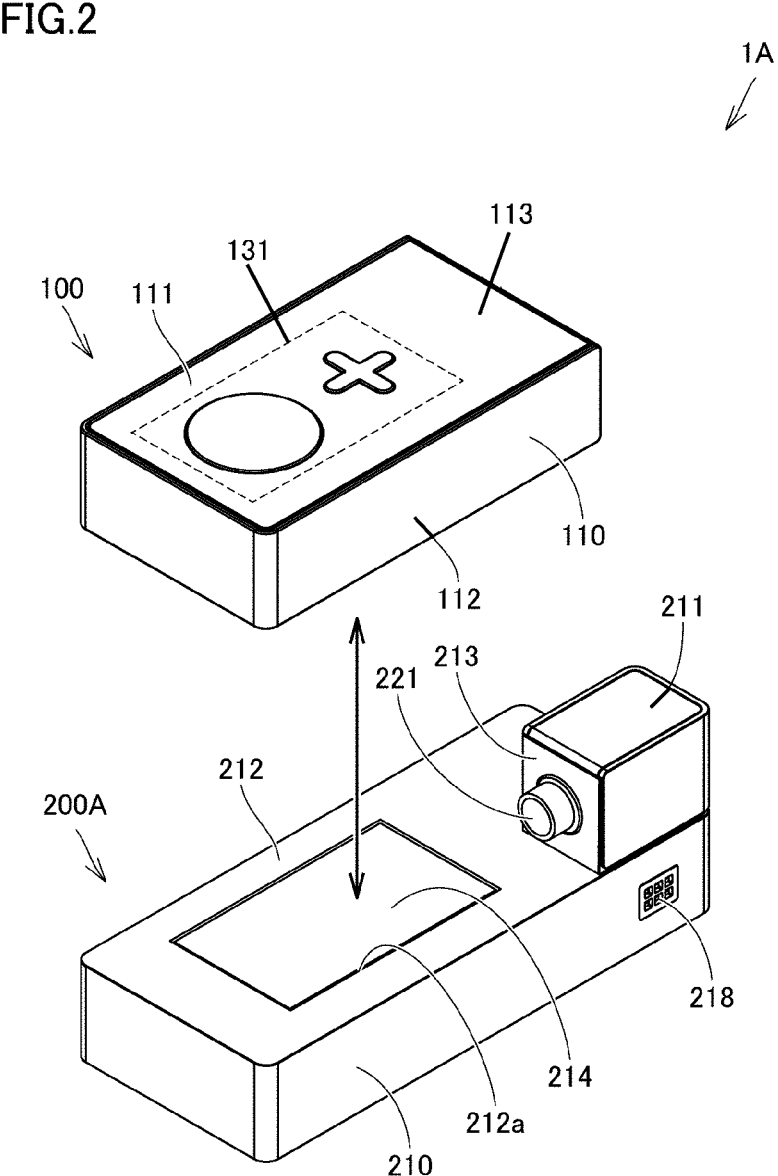
FIG. 2 is a perspective view of the attachment/detachment manner illustrated in FIG. 1 seen from a different angle.
Figure 3:
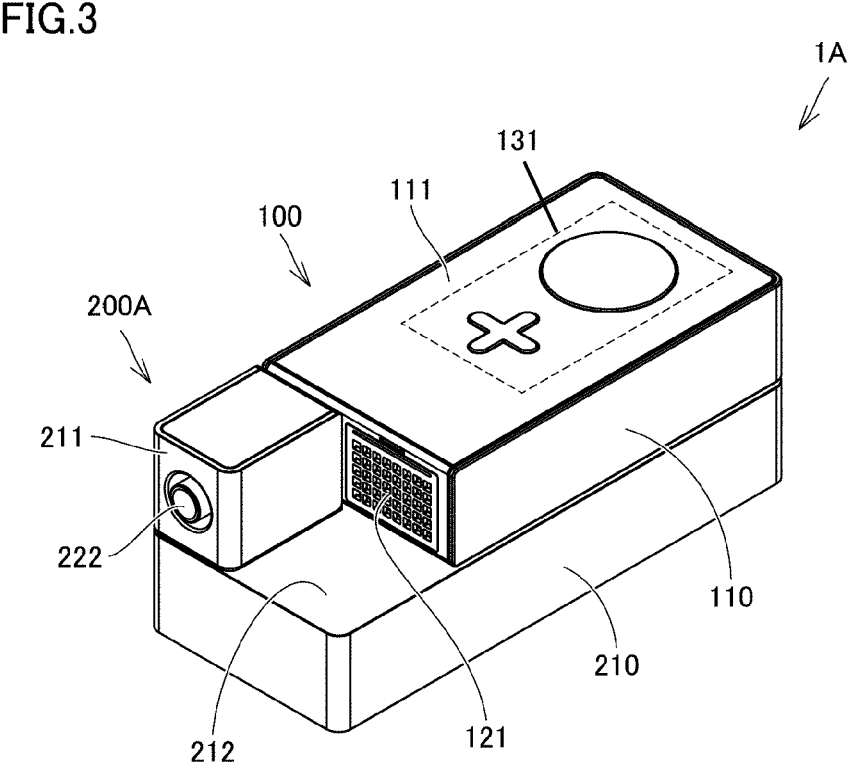
FIG. 3 is a perspective view illustrating a state in which the blowing unit is attached to the humidification unit in the CPAP device according to the first embodiment.

FIG. 1 is a perspective view illustrating an attachment/detachment manner of a blowing unit and a humidification unit of the CPAP device according to a first embodiment of the present disclosure. FIG. 2 is a perspective view of the attachment/detachment manner illustrated in FIG. 1 seen from a different angle. FIG. 3 is a perspective view illustrating a state in which the blowing unit is attached to the humidification unit in the CPAP device according to the present embodiment. First, with reference to these FIGS. 1 to 3, an outline of the structure and the attachment/detachment manner of a CPAP device 1A according to the present embodiment are described.

As illustrated in FIGS. 1 to 3, the CPAP device 1A includes a blowing unit 100 serving as a blowing device and a humidification unit 200A serving as the humidification device. Among these, the blowing unit 100 mainly includes a blower 140 (see FIGS. 5 to 7), and the humidification unit 200A is mainly provided with a tank chamber 216 and a vaporization chamber 217 (see FIGS. 6 and 7) included in a humidification mechanism.

The humidification unit 200A is configured such that the humidification unit 200A is attachable to and detachable from the blowing unit 100. Here, the CPAP device 1A according to the present embodiment is configured such that the CPAP device 1A can be used in two states, that is, a state in which the humidification unit 200A is attached to the blowing unit 100 and a state in which the humidification unit 200A is not attached to the blowing unit 100.

The purpose for this is to obtain high convenience not only for use, for example, at home but also for use, for example, away from home by configuring the CPAP device 1A such that the CPAP device 1A is divided into a plurality of units and these units are attachable to and detachable from each other. That is, for use, for example, at hole, the humidification unit 200A is attached to the blowing unit 100, thereby the CPAP device 1A can be used in the first use state to be described later, and for use, for example, away from home, the CPAP device 1A can be used in the second use state to be described later even when the humidification unit 200A is not attached to the blowing unit 100.

Here, the CPAP device 1A according to the present embodiment is configured such that the humidification unit 200A can be attached to the blowing unit 100 by placing the blowing unit 100 on the humidification unit 200A.

The blowing unit 100 has a substantially cuboid flat external shape, and an outer shell of the blowing unit 100 includes a first housing 110. The first housing 110 has an upper surface, a lower surface, and four side surfaces. In use, the upper surface and the lower surface are vertically arranged. Four side surfaces connect the upper surface and the lower surface to each other.

The upper surface of the first housing 110 is included in an operation surface 111 provided with an operation unit 131. The lower surface of the first housing 110 is included in a placement surface 112 to be placed on the humidification unit 200A in the first use state to be described later and to be placed on a floor, a table, or the like in the second use state to be described later. One of four side surfaces of the first housing 110 is included in a first connection surface 113 to be connected to the humidification unit 200A in the first use state to be described later.

The humidification unit 200A has a substantially cuboid elongated external shape, and an outer shell of the humidification unit 200A includes a second housing 210. The second housing 210 has an upper surface, a lower surface, and four side surfaces. In use, the upper surface and the lower surface are vertically arranged. Four side surfaces connect the upper surface and the lower surface to each. A projection that projects upward is provided in one of the four corners of the upper surface.

The lower surface of the second housing 210 is included in a placement surface to be placed on a floor, a table, or the like in the first use state to be described later. Part of the upper surface of the second housing 210 except for the above-described projection is included in a placement surface 212 on which the blowing unit 100 is to be placed in the first use state to be described later. A cavity 212a is provided at a predetermined position of the placement surface 212. The cavity 212a communicates with the tank chamber 216 to be described later and is for replenishment of the tank chamber 216 with water. A lid 214 is configured such that the lid 214 can be attached to the cavity 212a. Normally, the cavity 212a is closed by the lid 214.

One of the side surfaces of the above-described projection is included in a tube connection surface 211 to which an air tube 300 (see FIGS. 4A, 4B and 5) is connected in the first use state to be described later. Another of the side surfaces of the above-described projection is included in a second connection surface 213 to be connected to the blowing unit 100 in the first use state to be described later.

A first inlet 121 and a first outlet 122 are provided in the first connection surface 113 of the first housing 110. The first inlet 121 is for introduction of air from the outside of the first housing 110. The first outlet 122 is for delivery of the air from the inside of the first housing 110.

A second inlet 221 is provided in the second connection surface 213 of the second housing 210. The second inlet 221 is for introduction of the air from the outside of the second housing 210. A second outlet 222 is provided in the tube connection surface 211 of the second housing 210. The second outlet 222 is for delivery of the air from the inside of the second housing 210. An outside-air intake 218 is provided at a predetermined position of one of the side surfaces of the second housing 210. The outside-air intake 218 is for intake of the air from the outside of the second housing 210 to the vaporization chamber 217 to be described later provided in the second housing 210.

From the above description, in a state in which the humidification unit 200A is attached to the blowing unit 100 by placing the blowing unit 100 on the humidification unit 200A as illustrated in FIG. 3, the placement surface 112 of the first housing 110 is positioned so as to face the placement surface 212 of the second housing 210, and the first connection surface 113 of the first housing 110 is positioned so as to face the second connection surface 213 of the second housing 210. Thus, the first outlet 122 provided in the first connection surface 113 of the first housing 110 is connected to the second inlet 221 provided in the second connection surface 213 of the second housing 210. Even in this state, the first inlet 121 provided in the first housing 110 is not covered by the second housing 210 and open to the outside.

In contrast, in a state in which the humidification unit 200A is not attached to the blowing unit 100, the first connection surface 113 of the first housing 110 is exposed to the outside. Thus, both the first inlet 121 and the first outlet 122 provided in the first connection surface 113 of the first housing 110 are open outward.

Figure 4A:
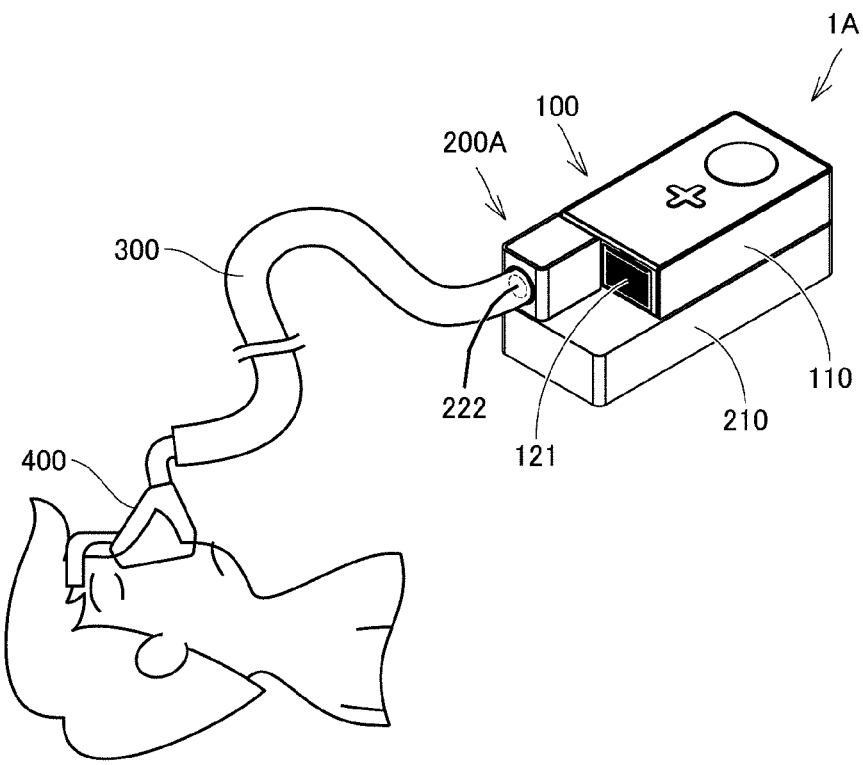
FIGS. 4A and 4B schematically illustrate a first use state and a second use state of the CPAP device according to the first embodiment.
Figure 4B:
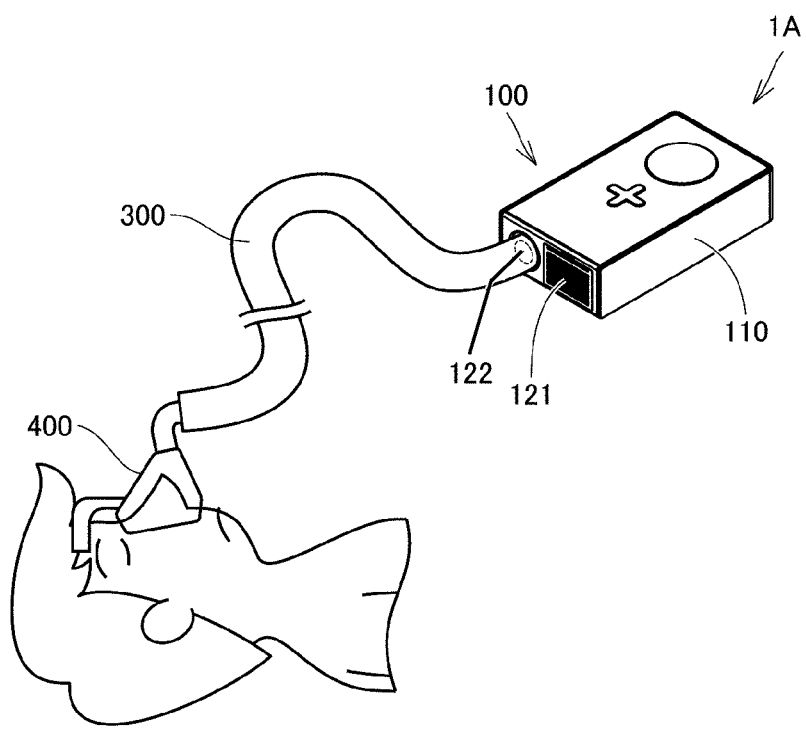

FIGS. 4A and 4B schematically illustrate use states of the CPAP device according to the present embodiment. FIG. 4A and FIG. 4B respectively illustrate the first use state and the second use state. Next, with reference to FIGS. 4A and 4B, the first use state and the second use state of the CPAP device 1A according to the present embodiment are described.

As illustrated in FIG. 4A, in the first use state, the CPAP device 1A is used in a state in which the humidification unit 200A is attached to the blowing unit 100 as described above. In this case, the air tube 300 is connected, at one end, to the second outlet 222 provided in the humidification unit 200A and, at another other end, to a mask 400.

Although the details will be described later, in the first use state, when the blower 140 provided in the blowing unit 100 is driven, the air is sucked from the first inlet 121 provided in the blowing unit 100 into the CPAP device 1A, and the sucked air is discharged from the second outlet 222 provided in the humidification unit 200A to the outside of the CPAP device 1A. In this way, the air discharged from the second outlet 222 is fed to the airway of the user through the air tube 300 and the mask 400.

As illustrated in FIG. 4B, in the second use state, the CPAP device 1A is used in a state in which the humidification unit 200A is not attached to the blowing unit 100 as described above. In this case, the air tube 300 is connected, at the one end, to the first outlet 122 provided in the blowing unit 100 and, at the other end, to the mask 400.

In the second use state, when the blower 140 provided in the blowing unit 100 is driven, the air is sucked from the first inlet 121 provided in the blowing unit 100 into the CPAP device 1A, and the sucked air is discharged from the first outlet 122 provided in the blowing unit 100 to the outside of the CPAP device 1A. In this way, the air discharged from the first outlet 122 is fed to the airway of the user through the air tube 300 and the mask 400.

Here, the mask 400 is put and attached such that, for example, the nose or mouth of the user is covered by the mask 400. The mask 400 having the shape and structure that fit the user can be selected from among various types of masks. The shapes and the structure of the mask 400 illustrated in FIGS. 4A and 4B are merely exemplary.

In order to prevent cessation of breathing during sleep, the CPAP device 1A continues to feed the air to the airway so as to open the airway while matching air feeding timing to respiratory timing of the user. For this purpose, the CPAP device 1A performs various types of control such as, for example, feedback control and feedforward control by a controller 130 (see FIG. 5) to be described later in accordance with the flow amount, pressure, and so forth detected by a flow amount sensor 133 and a pressure sensor 134 (see FIG. 5) to be described later in both the first use state and the second use state described above. In this way, the amount of feeding air or the like is adjusted by increasing or reducing the number of revolutions of the blower 140 so as to prevent the user from experiencing cessation of breathing during sleep.

Here, the CPAP device 1A according to the present embodiment has characteristic configurations mainly in the humidification unit 200A serving as the humidification device. Accordingly, the following description is specialized in the first use state in which the humidification unit 200A is used in addition to the blowing unit 100 out of the first use state and the second use state described above. Description of the second use state in which only the blowing unit 100 is used without using the humidification unit 200A is omitted.

Figure 5:
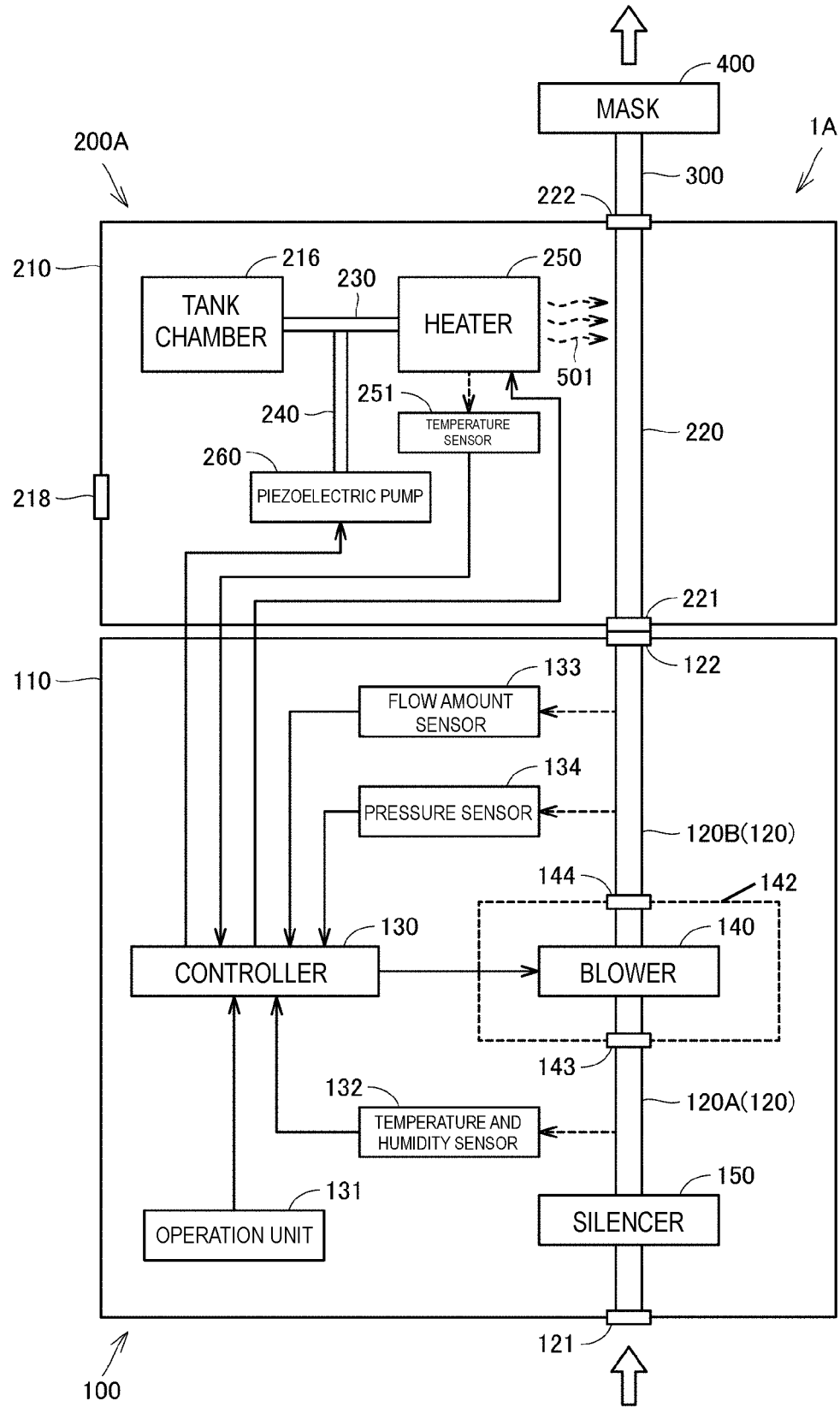
FIG. 5 illustrates the configuration of functional blocks of the CPAP device according to the first embodiment in the first use state.

FIG. 5 illustrates the configuration of functional blocks of the CPAP device according to the present embodiment in the first use state. Next, with reference to FIG. 5, the configuration of the functional blocks of the CPAP device 1A according to the present embodiment in the first use state is described.

As illustrated in FIG. 5, the CPAP device 1A includes the controller 130, the operation unit 131, a temperature and humidity sensor 132, the flow amount sensor 133, the pressure sensor 134, the blower 140, a silencer 150, the tank chamber 216, a heater 250, a temperature sensor 251, and a piezoelectric pump 260. Out of these, the controller 130, the operation unit 131, the temperature and humidity sensor 132, the flow amount sensor 133, the pressure sensor 134, the blower 140, and the silencer 150 are provided in the blowing unit 100, and the tank chamber 216, the heater 250, the temperature sensor 251, and the piezoelectric pump 260 are provided in the humidification unit 200A. The humidification unit 200A is also provided with a water supply passage 230 to be described later and an outside-air introduction passage 240 to be described later.

In addition to the first inlet 121 and the first outlet 122 described above, a first flow passage 120 is provided in the first housing 110 of the blowing unit 100. The first flow passage 120 is configured such that the first flow passage 120 connects the first inlet 121 and the first outlet 122 to each other.

The blower 140 is provided in the first flow passage 120. The blower 140 includes, for example, a centrifugal fan. The blower 140 is installed in a blower chamber 117 (see FIGS. 6 and 7) to be described later provided in the first housing 110. In this way, the blower 140 is disposed in the first flow passage 120.

Here, the blower 140 includes a casing 142 in which a suction port 143 and a discharge port 144 of the blower 140 are provided. With this structure, the first flow passage 120 includes an upstream flow passage portion 120A and a downstream flow passage portion 120B. The upstream flow passage portion 120A connects the first inlet 121 provided in the first housing 110 and the suction port 143 provided in the blower 140 to each other. The downstream flow passage portion 120B connects the discharge port 144 provided in the blower 140 and the first outlet 122 provided in the first housing 110 to each other.

The silencer 150 is provided in the upstream flow passage portion 120A being a portion of the first flow passage 120 positioned between the first inlet 121 and the suction port 143. The silencer 150 is for suppressing the leakage of the noise generated by the blower 140 (operating sound of a drive motor included in the blower 140, wind noise, and so forth) to the outside through the first inlet 121. The details of the silencer 150 will be described later.

In addition to the second inlet 221, the second outlet 222, and the outside-air intake 218 described above, a second flow passage 220 is provided in the second housing 210 of the humidification unit 200A. The second flow passage 220 is configured such that the second flow passage 220 connects the second inlet 221 and the second outlet 222 to each other.

In the second flow passage 220, the air passing through the second flow passage 220 is humidified by the humidification mechanism to be described later. Thus, in the first use state, an appropriate degree of moisture (that is, water vapor 501 represented by the wavy broken line arrows in the drawing) is added to the air to be fed to the airway of the user.

As described above, the water supply passage 230 and the outside-air introduction passage 240 are provided in the humidification unit 200A. The water supply passage 230 connects the tank chamber 216 serving as a reservoir and the heater 250 serving as a vaporizer to each other. The water supply passage 230 is for feeding the water stored in the tank chamber 216 to the heater 250 therethrough. The outside-air introduction passage 240 serving as a gas introduction passage connects the piezoelectric pump 260 serving as a gas introduction source and the water supply passage 230 to each other. Although the details of the outside-air introduction passage 240 will be described later, the outside-air introduction passage 240 is utilized to feed the water stored in the tank chamber 216 to the heater 250.

The heater 250 vaporizes the water supplied thereto by heating the water. The piezoelectric pump 260 is an air pump for pumping the air. Although the details of the piezoelectric pump 260 will be described later, the piezoelectric pump 260 introduces the outside air having been taken from the above-described outside-air intake 218 to the vaporization chamber 217 into the water supply passage 230 through the outside-air introduction passage 240, thereby feeding the water stored in the tank chamber 216 to the heater 250.

As main elements, the controller 130 includes, for example, a central processing unit (CPU) that executes programs, ROM (read only memory)/RAM (random-access memory), various drivers that drive the blower 140, the heater 250, and the piezoelectric pump 260, and a computing unit that performs various types of computing in accordance with various types of information inputted from the temperature and humidity sensor 132, the flow amount sensor 133, the pressure sensor 134, and the temperature sensor 251. The ROM/RAM includes ROM that stores, in a non-volatile manner, data and RAM that stores, in a volatile manner, data generated when the CPU executes the programs or data inputted through the operation unit 131. The elements of the controller 130 are connected to each other through a data bus.

Processes in the CPU are realized by software to be executed by various types of hardware and the CPU. Such software is stored in the ROM/RAM in advance. Reception of operations in the operation unit 131, control of the drive motor that drives the blower 140, control of the heater 250, control of the piezoelectric pump 260, the above-described various types of computing, and so forth are also realized by the software.

Power is suppled to the controller 130, the blower 140, the heater 250, the piezoelectric pump 260, and so forth by an internal power source (not illustrated) or an external power source (not illustrated). For connection to the external power source, for example, an alternating current (AC) adapter (not illustrated) or the like is used.

The temperature and humidity sensor 132 is for measurement of the temperature and humidity of the air that has been introduced from the outside into the CPAP device 1A and that is to be fed later to the airway of the user. The temperature and humidity sensor 132 is provided in the upstream flow passage portion 120A of the first flow passage 120. The temperature and humidity of the air detected by the temperature and humidity sensor 132 are outputted to the controller 130 so as to be utilized mainly for humidification operation with the humidification mechanism.

The flow amount sensor 133 is for measurement of the flow amount of the air between the CPAP device 1A and the air tube 300. The pressure sensor 134 is for measurement of the pressure of the air fed by the blower 140. The flow amount sensor 133 and the pressure sensor 134 correspond to a respiratory state detector and are provided in the downstream flow passage portion 120B of the first flow passage 120.

Although the detailed description is omitted here, the flow amount and the pressure detected by the flow amount sensor 133 and the pressure sensor 134 are outputted to the controller 130. The controller 130 performs control such as, for example, feedback control and feedforward control in accordance with the flow amount, the pressure, and the like, thereby increasing or reducing the number of revolutions of the blower 140. The flow amount and the pressure of the air detected by the flow amount sensor 133 and the pressure sensor 134 are also utilized for the humidification operation with the humidification mechanism.

The temperature sensor 251 is for measurement of the temperature of the heater 250 and provided adjacent to the heater 250. The temperature of the heater 250 detected by the temperature sensor 251 is outputted to the controller 130 and is mainly utilized for the humidification operation with the humidification mechanism.

The CPAP device 1A may be additionally provided with a display that includes a liquid crystal display (LCD) or an organic electro-luminescence (EL) display. Here, the display may be provided in the blowing unit 100 or the humidification unit 200A. The operation unit 131 is not necessarily a button having a physical shape as illustrated in FIGS. 1 to 3. The operation unit 131 may be, for example, a touch panel or the like provided in a display surface of the LCD. Buttons of the operation unit 131 other than a button with which the power of the CPAP device 1A is turned on/off may be provided in the humidification unit 200A.

Here, as illustrated in FIG. 5, in the first use state, the first outlet 122 provided in the first housing 110 and the second inlet 221 provided in the second housing 210 are connected to each other. Thus, in the first use state, the second flow passage 220 is connected to the downstream side of the first flow passage 120.

Accordingly, in the first use state, when the blower 140 is driven, the air sucked from the first inlet 121 passes through the first flow passage 120 and the second flow passage 220 in this order and is discharged from the second outlet 222. The air discharged from the second outlet 222 is then fed to the airway of the user through the air tube 300 and the mask 400. That is, in this first use state, the first inlet 121 functions as an air suction port from which the air is sucked into the CPAP device 1A, and the second outlet 222 functions as an air discharge port from which the air is discharged from the inside of the CPAP device 1A.

Figure 6:
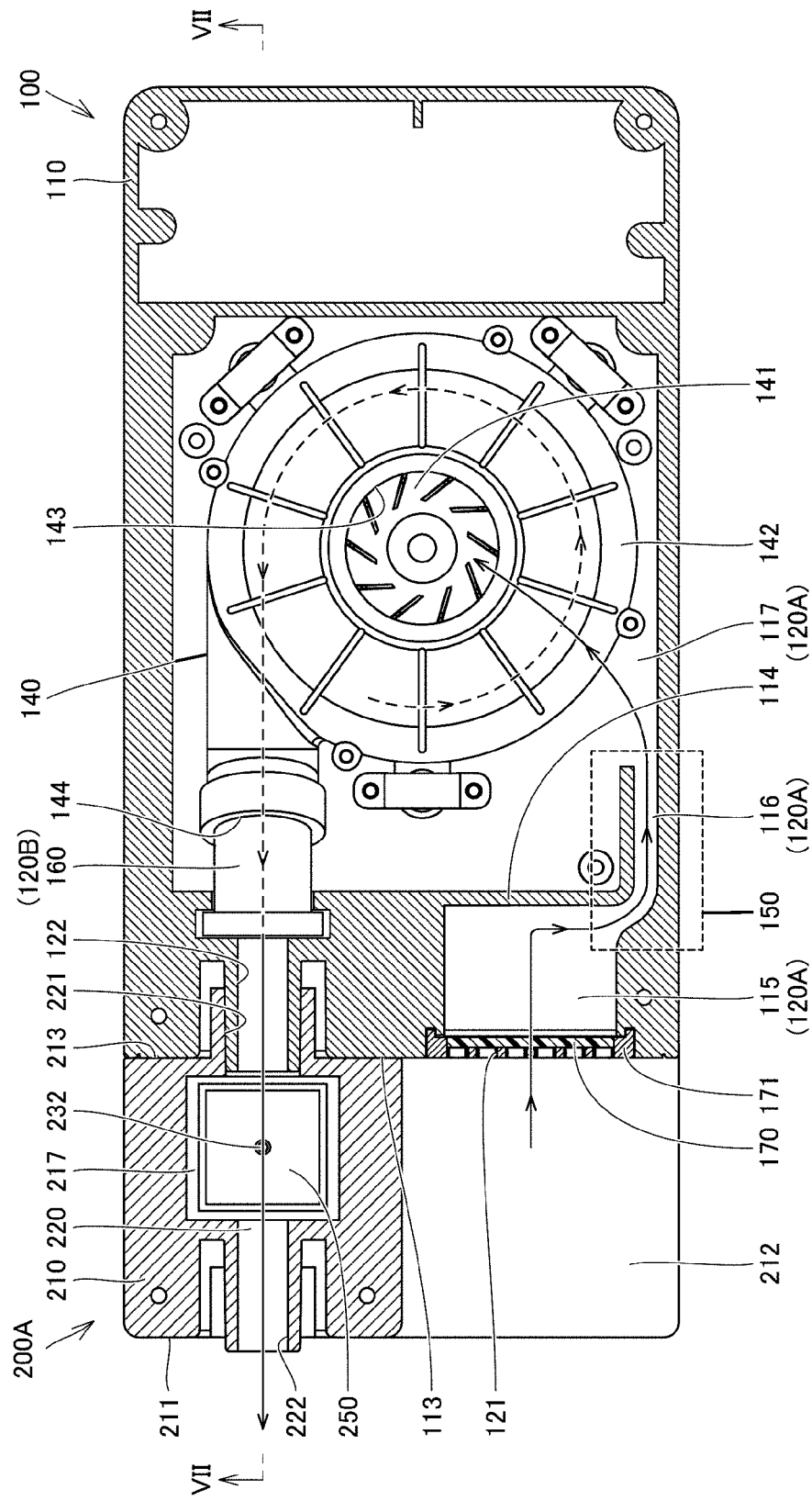
FIG. 6 is a schematic sectional view of the CPAP device according to the first embodiment in the first use state.
Figure 7:
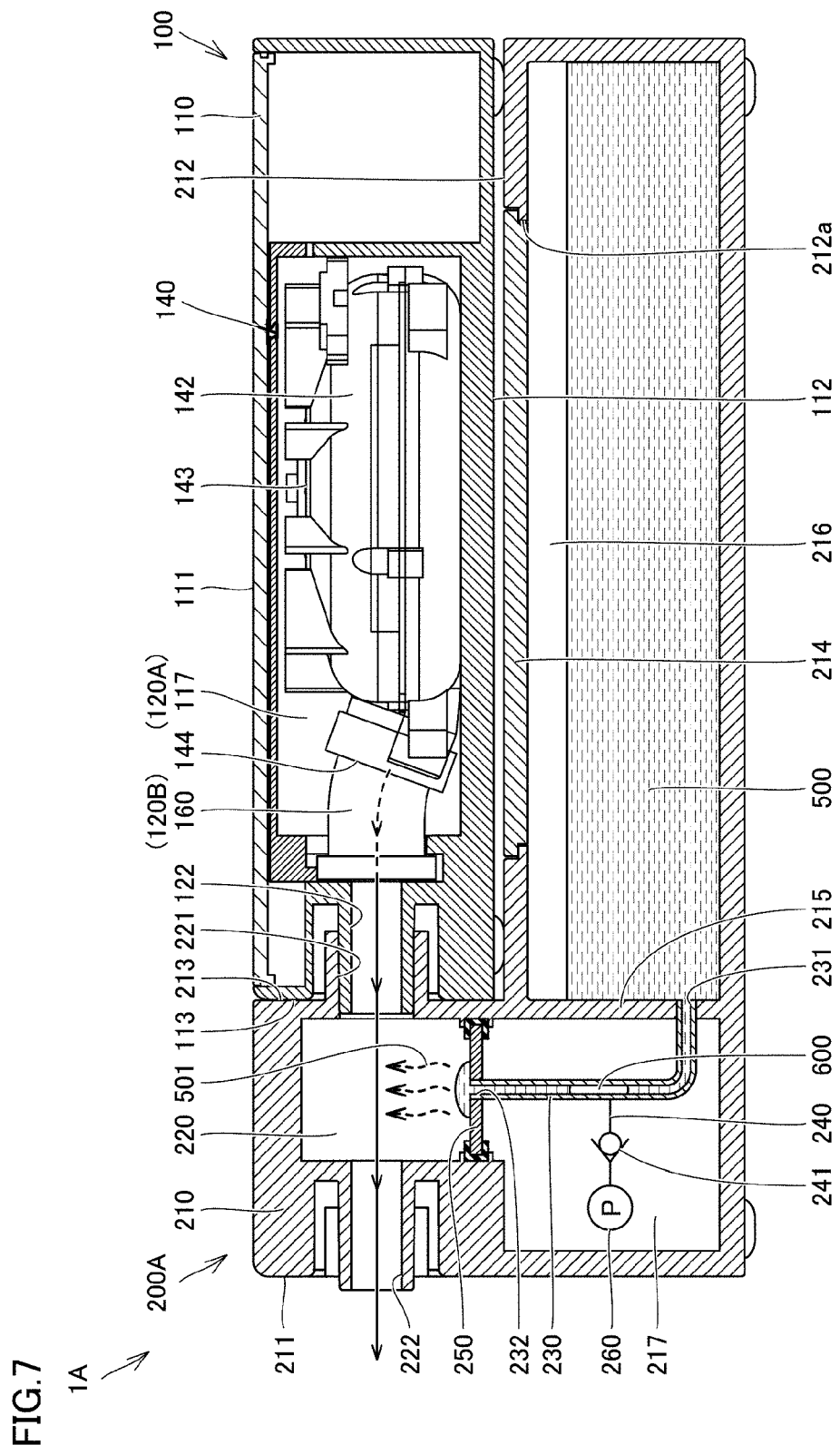
FIG. 7 is a schematic sectional view taken along line VII-VII illustrated in FIG. 6.

FIG. 6 is a schematic sectional view of the CPAP device according to the present embodiment in the first use state. FIG. 7 is a schematic sectional view taken along line VII-VII illustrated in FIG. 6. Hereafter, with reference to FIGS. 6 and 7, the detailed structure of the CPAP device 1A according to the present embodiment and airflow inside the CPAP device 1A in the first use state are described. In FIGS. 6 and 7, the airflow generated when the blower 140 is operated is schematically illustrated by arrows.

As illustrated in FIGS. 6 and 7, a space inside the first housing 110 of the blowing unit 100 is separated into a plurality of chambers by providing various wall portions, a hose, and so forth. The plurality of chambers include a wide portion 115, a narrow portion 116, and the blower chamber 117. The wide portion 115, the narrow portion 116, and the blower chamber 117 correspond to the above-described upstream flow passage portion 120A.

As illustrated in FIG. 6, the wide portion 115 is provided adjacent to the first inlet 121 provided in the first connection surface 113 of the first housing 110. The sectional area perpendicular to a flowing direction of the air in the wide portion 115 is made to be relatively large so as to reduce pressure loss that can occur in the first inlet 121. The sectional area perpendicular to the flowing direction of the air is made to be greater in the wide portion 115 than in the narrow portion 116 to be described later.

A filter 170 is installed in the first inlet 121 to capture foreign matter such as dust contained in the air. In order to secure the filter 170 to the first connection surface 113, a filter cover 171 being part of the first housing 110 is attached to the first connection surface 113. The filter cover 171 has a plurality of holes arranged in a matrix shape. The plurality of holes are included in the first inlet 121.

The narrow portion 116 is provided adjacent to the wide portion 115. The narrow portion 116 is formed by providing a separation wall 114 in the first housing 110 and made to have a relatively small sectional area perpendicular to the flowing direction of the air. The sectional area perpendicular to the flowing direction of the air is made to be smaller in the narrow portion 116 than in the above-described wide portion 115.

The blower chamber 117 is provided adjacent to the narrow portion 116 and accommodates therein the blower 140. The blower chamber 117 is made to have a relatively large sectional area perpendicular to the flowing direction of the air and have a comparatively large space that occupies most of the space in the first housing 110. The sectional area perpendicular to the flowing direction of the air is made to be greater in the blower chamber 117 than in the above-described narrow portion 116.

Here, a portion of the first flow passage 120 corresponding to the wide portion 115, the narrow portion 116, and the blower chamber 117 is a region in which the sectional area perpendicular to the flowing direction of the air is sharply increased and reduced from the downstream side toward the upstream side in the flowing direction of the air. This region functions as the above-described silencer 150. With the silencer 150 configured as above, the noise generated in the blower 140 is attenuated by, for example, the diffuse reflection of the noise during the passage of the noise through the silencer 150. As a result, the leakage of the noise through the first inlet 121 can be suppressed.

As illustrated in FIGS. 6 and 7, the blower 140 includes, for example, a centrifugal fan and is secured to a wall portion (that is, a base plate portion) in a state in which the blower 140 is accommodated in the blower chamber 117. This wall portion defines the placement surface 112 of the first housing 110. The blower 140 includes an impeller 141, the drive motor not appeared in the drawing, and the casing 142.

The impeller 141 is secured to a rotating shaft of the drive motor. Thus, when the drive motor is driven, the impeller 141 rotates. When the impeller 141 rotates, the air is agitated so as to apply the centrifugal force to the air. This generates an air current in the casing 142, thereby sucking the air from the suction port 143 provided in the casing 142 and discharging the air from the discharge port 144 provided in the casing 142.

The suction port 143 of the blower 140 is provided at a portion of the casing 142 positioned above a shaft portion of the impeller 141 and disposed so as to face a wall portion that defines the operation surface 111 of the first housing 110 (that is, a top plate portion) so as to be separated from an inner surface of the wall portion by a predetermined distance. Meanwhile, the discharge port 144 of the blower 140 is provided at a portion of the casing 142 positioned in a tangential direction of an outer edge of the impeller 141 when seen along the shaft portion of the impeller 141 and disposed so as to be separated from the impeller 141 by a predetermined distance.

Here, the suction port 143 of the blower 140 communicates with the blower chamber 117. The discharge port 144 of the blower 140 is disposed so as to cross the blower chamber 117, and one end of the discharge port 144 is connected to another end of a hose 160 connected to the first outlet 122 provided in the first housing 110. A space inside the hose 160 corresponds to the above-described downstream flow passage portion 120B.

The first outlet 122 is provided in the first connection surface 113 of the first housing 110. The first outlet 122 has a nozzle shape so as to allows both the second inlet 221 provided in the second connection surface 213 of the second housing 210 and the air tube 300 to be connected thereto.

As illustrated in FIGS. 6 and 7, a space inside the second housing 210 of the humidification unit 200A is separated into the tank chamber 216 and the vaporization chamber 217 by providing a partition 215. Out of these, part of the vaporization chamber 217 corresponds to the above-described second flow passage 220.

The tank chamber 216 is defined by wall portions of the second housing 210 including the partition 215 and corresponds to the reservoir in which water 500 is stored. The tank chamber 216 is positioned below the cavity 212a provided in the placement surface 212 being the upper surface of the second housing 210 and communicates with the cavity 212a. As described above, the cavity 212a is closed by the lid 214, thereby leakage of water is prevented. Packing or the like may be provided between a wall surface of the second housing 210 defining the cavity 212a and the lid 214 so as to ensure liquid tightness at this portion. Here, an air introduction port may be provided in a portion of the wall portions defining the tank chamber 216 to introduce the air into the tank chamber 216 when the amount of the water 500 stored in the tank chamber 216 is reduced.

The vaporization chamber 217 is defined by wall portions of the second housing 210 including the partition 215 and provided so as to include as part thereof the above-described projection provided on the upper surface of the second housing 210. The water supply passage 230, the outside-air introduction passage 240, the heater 250, the piezoelectric pump 260, and so forth are disposed in the vaporization chamber 217. Out of these, the heater 250 is installed in a lower portion of a space inside the above-described projection. Thus, the vaporization chamber 217 is separated into a space above the heater 250 and a space below the heater 250. The space above the heater 250 corresponds to the above-described second flow passage 220.

The space above the heater 250 corresponding to the second flow passage 220 communicates with the first flow passage 120 provided in the first housing 110 through the second inlet 221 provided in the second connection surface 213 of the second housing 210 and the first outlet 122 provided in the first connection surface 113 of the first housing 110. This space above the heater 250 corresponding to the second flow passage 220 also communicates with the second outlet 222 provided in the tube connection surface 211 of the second housing 210. The second outlet 222 has a nozzle shape so as to allow the air tube 300 to be connected thereto.

The water supply passage 230 includes a pipe bent into a substantially L shape. One end portion of the water supply passage 230 penetrates through the partition 215 and is connected to the tank chamber 216, and another end portion of the water supply passage 230 is connected to the heater 250 from below. Here, the heater 250 includes a heating plate. The other end portion of the water supply passage 230 is disposed such that the other end portion of the water supply passage 230 penetrates through the heating plate so as to face the second flow passage 220.

The above-described one end portion of the water supply passage 230 corresponds to a water supply port 231 that allows the water 500 stored in the tank chamber 216 to be supplied toward the water supply passage 230 therethrough. The above-described other end portion of the water supply passage 230 corresponds to a water discharge port 232 that allows the water 500 having been supplied to the water supply passage 230 through the water supply port 231 to be discharged toward the heater 250 therethrough. Although the water supply port 231 is disposed below the water discharge port 232 here, when the inner diameter of the above-described pipe included in the water supply passage 230 is set to, for example, greater than 0.1 mm and smaller than 1.0 mm, the water 500 stored in the tank chamber 216 flows into the water supply passage 230 due to so-called capillarity. In this way, the water supply passage 230 is normally maintained in a state in which the water supply passage 230 is filled with the water 500.

The outside-air introduction passage 240 includes a pipe and is connected to an intermediate position of the water supply passage 230 so as to allow outside air 600 to be introduced to the intermediate position of the water supply passage 230. An end of the outside-air introduction passage 240 opposite to the connection to the water supply passage 230 is connected to the piezoelectric pump 260.

The outside-air introduction passage 240 is provided with a check valve 241 serving as a penetration preventer that prevents the water from entering the piezoelectric pump 260 from the water supply passage 230. The check valve 241 allows movement of the outside air 600 from the piezoelectric pump 260 toward the water supply passage 230 and limits movement of the outside air 600 and the water 500 from the water supply passage 230 toward the piezoelectric pump 260. Instead of the check valve 241, the penetration preventer may include a waterproof breathable membrane. In the case where the penetration preventer includes a waterproof breathable membrane, the movement of the outside air 600 from the piezoelectric pump 260 toward the water supply passage 230 is allowed, and the movement of the water 500 from the water supply passage 230 toward the piezoelectric pump 260 is limited.

The piezoelectric pump 260 is an air pump that includes a diaphragm pump for which electrostrictive characteristics of a thin plate-shaped piezoelectric material is utilized and that can suck and discharge the air as described above. With this, the outside air 600 taken to the vaporization chamber 217 through the outside-air intake 218 provided in the second housing 210 is sucked and discharged toward the outside-air introduction passage 240, thereby allowing the outside air 600 to be introduced to the above-described intermediate position of the water supply passage 230.

Here, mainly, the above-described elements, that is, the tank chamber 216, the water supply passage 230, the outside-air introduction passage 240, the heater 250, and the piezoelectric pump 260 are included in the humidification mechanism that humidifies the air serving as a heating target gas blown by the blower 140. The humidification operation with the humidification mechanism is basically realized by a plurality of times of vaporization operation to be repeatedly performed when the piezoelectric pump 260 is driven in an intermittent manner. Due to the vaporization operation, the water 500 having been supplied to the heater 250 is heated and vaporized, thereby the water vapor 501 is generated in the space of the vaporization chamber 217 above the heater 250 (that is, the second flow passage 220). Humidification is performed by adding the generated water vapor 501 to the air passing through this space. The vaporization operation and the humidification operation having been described will be described in detail later.

Thus, in the first use state, as described above, the air sucked from the first inlet 121 passes through the first flow passage 120 and the second flow passage 220 in this order, is discharged from the second outlet 222, and is fed to the airway of the user through the air tube 300 connected to the second outlet 222 and the mask 400 connected to the air tube 300. In so doing, when the water vapor 501 is added to the air in the second flow passage 220, the air is appropriately humidified so as to be fed to the airway of the user.

FIGS. 8A to 8D include schematic views for description of the vaporization operation in the CPAP device according to the present embodiment. Next, with reference to FIGS. 8A to 8D, the vaporization operation in the CPAP device 1A according to the present embodiment will be described in detail. Each of FIGS. 8A to 8D sequentially illustrates a single vaporization operation, and the vaporization operation proceeds in the order of FIG. 8A to FIG. 8D.

Figure 8A:
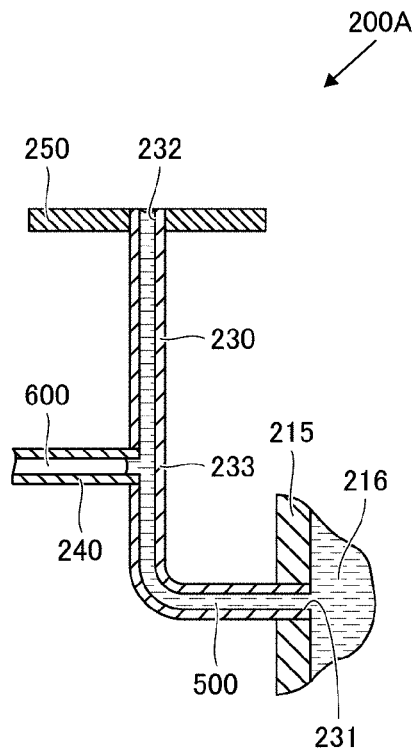
FIGS. 8A to 8D include schematic views for description of vaporization operation in the CPAP device according to the first embodiment.

First, as illustrated in FIG. 8A, before the start of the vaporization operation, the water 500 stored in the tank chamber 216 flows into the water supply passage 230 through the water supply port 231 in accordance with the above-described capillarity. Thus, the water supply passage 230 is filled with the water 500 having flowed thereinto. At this time, the water 500 having flowed into the water supply passage 230 stops at the water discharge port 232 due to the surface tension thereof. Thus, the water 500 is not supplied to the heater 250. At this time, due to the function of the check valve 241 provided in the outside-air introduction passage 240, the water 500 does not penetrate into the outside-air introduction passage 240, either.

Figure 8B:
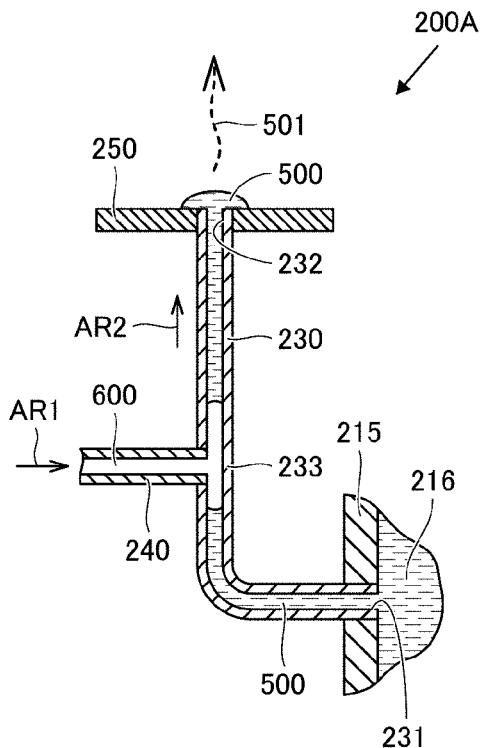

Next, as illustrated in FIG. 8B, the piezoelectric pump 260 is driven to start the vaporization operation. As a result, as indicated by an arrow AR1 in the drawing, the outside air 600 is introduced to an intermediate position 233 of the water supply passage 230 through the outside-air introduction passage 240. When the outside air 600 is introduced, the water 500 with which a portion of the water supply passage 230 between the intermediate position 233 and the water discharge port 232 is filled receives the pressure of the outside air 600 so as to be moved in an arrow AR2 direction in the drawing. Thus, the water 500 is pushed out through the water discharge port 232, thereby supplying of the water 500 to the heater 250 is started. The water supplied to the heater 250 is instantaneously heated by the heater 250 and vaporized so as to become the water vapor 501 and added to the air passing through the second flow passage 220.

Figure 8C:
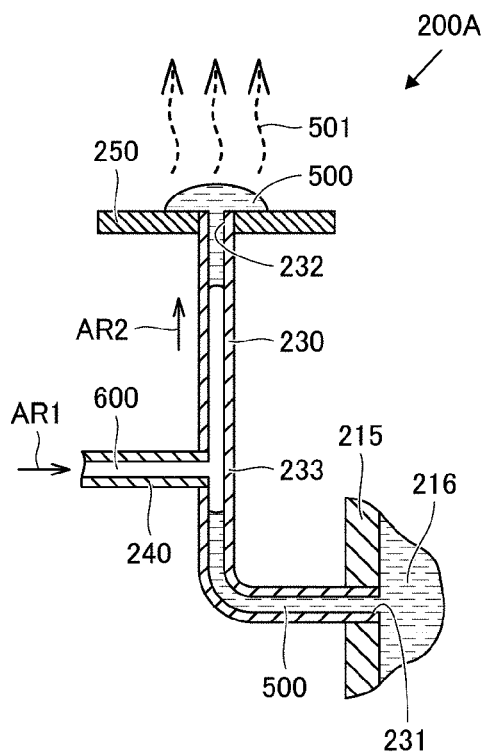

Subsequently, as illustrated in FIG. 8C, a more amount of the outside air 600 is introduced into the water supply passage 230 due to the drive of the piezoelectric pump 260. Thus, the water 500 is sequentially pushed out so as to be supplied to the heater 250, and accordingly, generation of the water vapor 501 continues. At this time, the outside air 600 having been introduced into the water supply passage 230 is also gradually moved to the water discharge port 232 side in the arrow AR2 direction in the drawing.

Figure 8D:
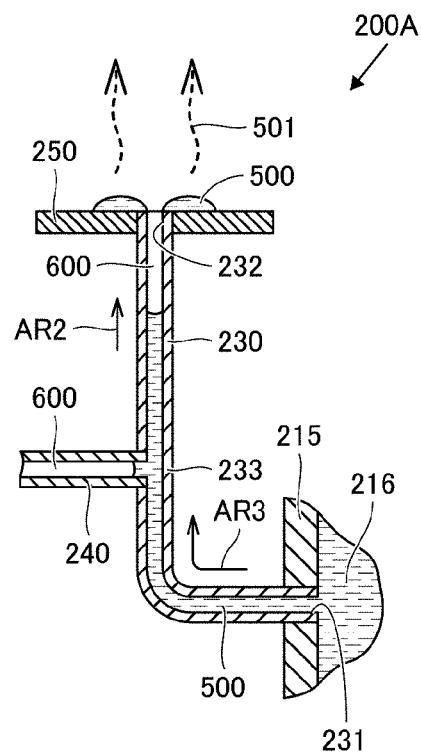

Next, as illustrated in FIG. 8D, after a certain period of time has elapsed from the start of the drive of the piezoelectric pump 260, the drive of the piezoelectric pump 260 is stopped. This causes the introduction of the outside air 600 to the intermediate position 233 to stop, and, due to the capillarity, the water 500 flows again from the tank chamber 216 into the water supply passage 230 through the water supply port 231 in an arrow AR3 direction in the drawing. At this time, all the outside air 600 having been introduced from the intermediate position 233 into the water supply passage 230 is pushed out through the water discharge port 232 by the water 500 having flowed into the water supply passage 230. Along with this, all the water 500 with which the portion of the water supply passage 230 between the intermediate position 233 and the water discharge port 232 has been filled at the start of the vaporization operation is also pushed out through the water discharge port 232 and vaporized by the heater 250.

When the above-described process has been performed, a single vaporization operation is completed. In order to vaporize all the water 500 with which the portion of the water supply passage 230 between the intermediate position 233 and the water discharge port 232 is filled at the start of the vaporization operation as described above, it is sufficient that the outside air 600 having a volume larger than or equal to the volume of this portion of the water supply passage 230 be introduced into the water supply passage 230 with the piezoelectric pump 260.

Figure 9C:
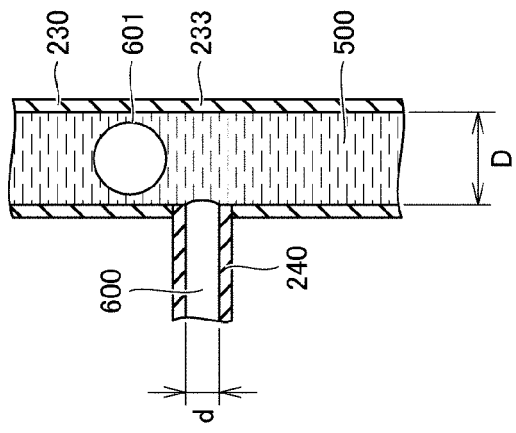
FIGS. 9A to 9C include schematic views for description of a principle of the vaporization operation of the CPAP device according to the first embodiment.
Figure 9B:
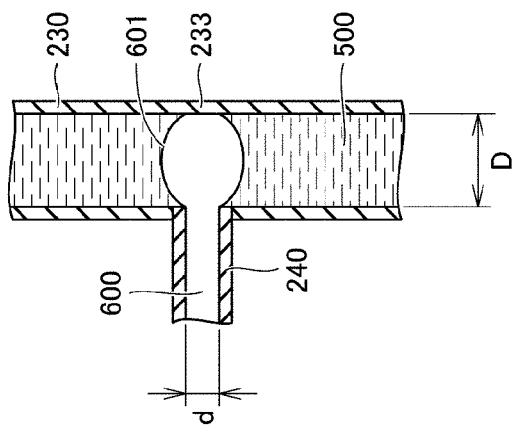
Figure 9A:
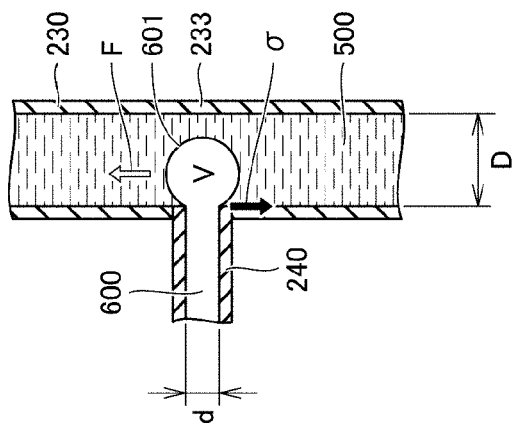

FIGS. 9A to 9C include schematic views for description of a principle of the above-described vaporization operation. Next, with reference to FIGS. 9A to 9C, the principle of the above-described vaporization operation will be described in detail.

In order to push out the water 500 from the water discharge port 232 by the outside air 600 having been introduced into the water supply passage 230, it is required that the introduced outside air 600 do not become a fine bubble and the water 500 be reliably separated by the outside air 600 at the intermediate position 233 of the water supply passage 230. When the introduced outside air 600 becomes a fine bubble, the fine bubble floats upward in the water supply passage 230 and is discharged from the water discharge port 232 while a pressure sufficient to push out the water 500 from the water discharge port 232 is not being obtained. In order for this outside air 600 not becoming a fine bubble, it is required that the following points be considered.

That is, as illustrated in FIG. 9A, the outside air 600 having been introduced to the intermediate position 233 of the water supply passage 230 becomes a bubble 601 having a substantially spherical shape in a portion of the water supply passage 230 connected to the outside-air introduction passage 240. This bubble 601 gradually increases in size. A floating force F acts on this bubble 601 as illustrated in the drawing, and a surface tension σ acts on a portion of the water 500 in contact with the bubble 601.

When the surface tension σ is greater than or equal to the floating force F (that is, when a condition σ≥F is satisfied), the bubble 601 is connected to the outside air 600 in the outside-air introduction passage 240 and stops at the intermediate position 233 of the water supply passage 230, and an increase in a volume V of the bubble 601 proceeds. In contrast, when the surface tension σ is smaller than the floating force F (that is, when a condition σ<F is satisfied), the bubble 601 is separated from the outside air 600 in the outside-air introduction passage 240, becomes the fine bubble 601, and floats upward in the water supply passage 230.

Thus, when the increase in the volume V of the bubble 601 proceeds and the diameter of the bubble 601 reaches an inner diameter D of the water supply passage 230 as illustrated in FIG. 9B while the above-described condition σ≥F being satisfied, the water 500 is reliably separated by the introduced outside air 600 at the intermediate position 233 without the bubble 601 becoming a fine bubble and being separated from the outside air 600 in the outside-air introduction passage 240 and also without the outside air 600 introduced into the water supply passage 230 thereafter becoming a fine bubble. As a result, in this case, the water 500 is pushed out from the water discharge port 232 by the outside air 600 introduced into the water supply passage 230, and accordingly, an intended vaporization operation can be reliably performed.

In contrast, when the above-described condition σ<F becomes satisfied before the diameter of the bubble 601 reaches the inner diameter D of the water supply passage 230, the bubble 601 is separated from the outside air 600 in the outside-air introduction passage 240 and becomes the fine bubble 601 so as to float upward in the water supply passage 230 as illustrated in FIG. 9C. As a result, in this case, the water 500 is not pushed out from the water discharge port 232 by the outside air 600 introduced into the water supply passage 230. Accordingly, the intended vaporization operation is not reliably performed.

Here, the floating force F is proportional to the volume V of the bubble 601, and the surface tension σ is proportional to an inner diameter d of the outside-air introduction passage 240. Meanwhile, the increase in the volume V of the bubble 601 is limited by the inner diameter D of the water supply passage 230. Accordingly, whether the outside air 600 introduced into the water supply passage 230 becomes a small bubble is determined based on an inner diameter rate D/d between the inner diameter D of the water supply passage 230 and the inner diameter d of the outside-air introduction passage 240.

Accordingly, when the above-described inner diameter rate D/d is appropriately set, the intended vaporization operation can be reliably performed. Although a specific value of the above-described inner diameter rate D/d with which the outside air 600 introduced into the water supply passage 230 does not become a fine bubble depends on the size of the inner diameter D of the water supply passage 230, for example, in a range of 0.1 mm≤D≤1 mm being an approximate size of the inner diameter D of the water supply passage 230 with which the capillarity can be obtained, the inner diameter rate D/d is about 2.9≤D/d≤13.4.

Figure 10:
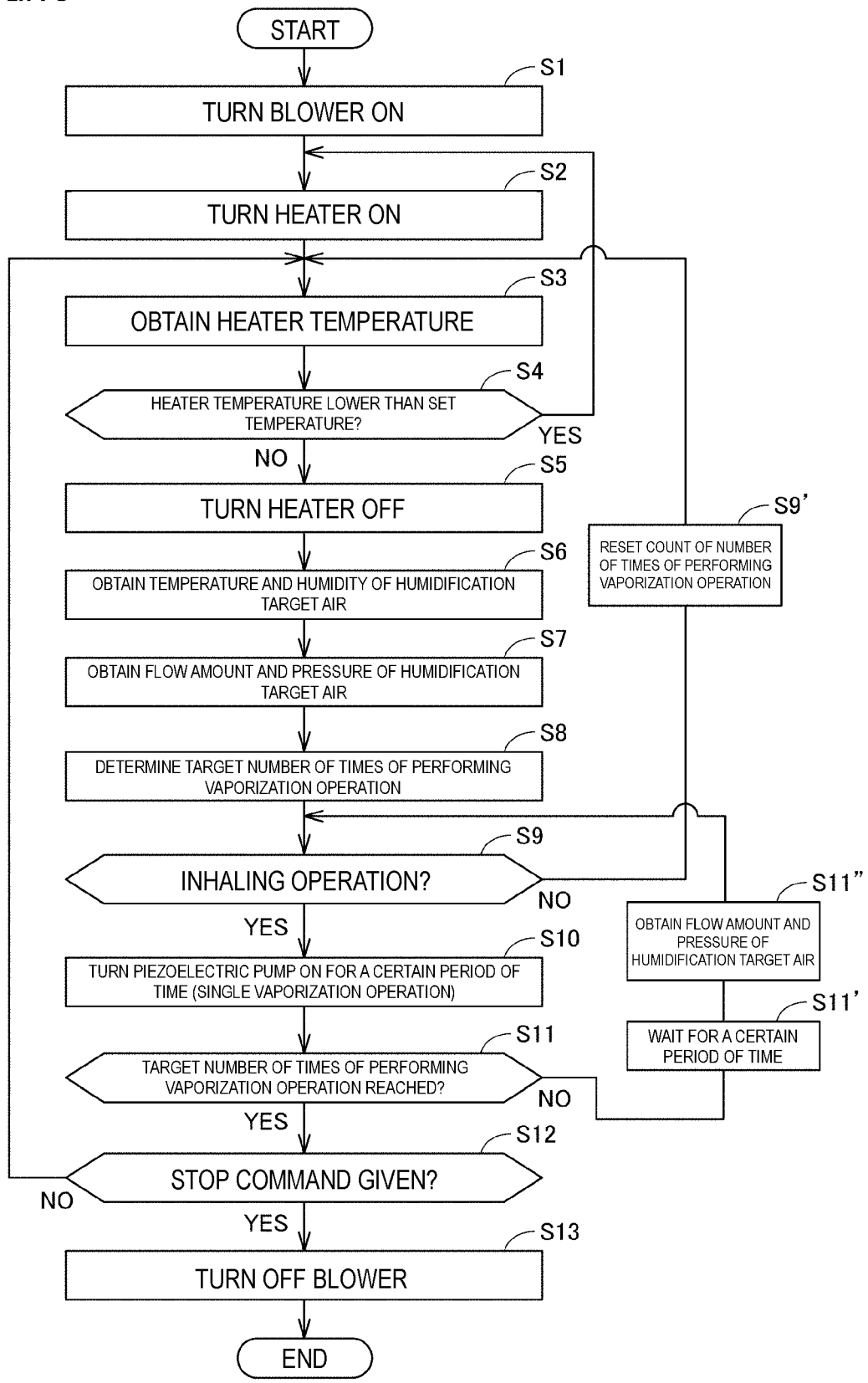
FIG. 10 is a flowchart illustrating operation of a controller of the CPAP device according to the first embodiment in the first use state.
Figure 11:
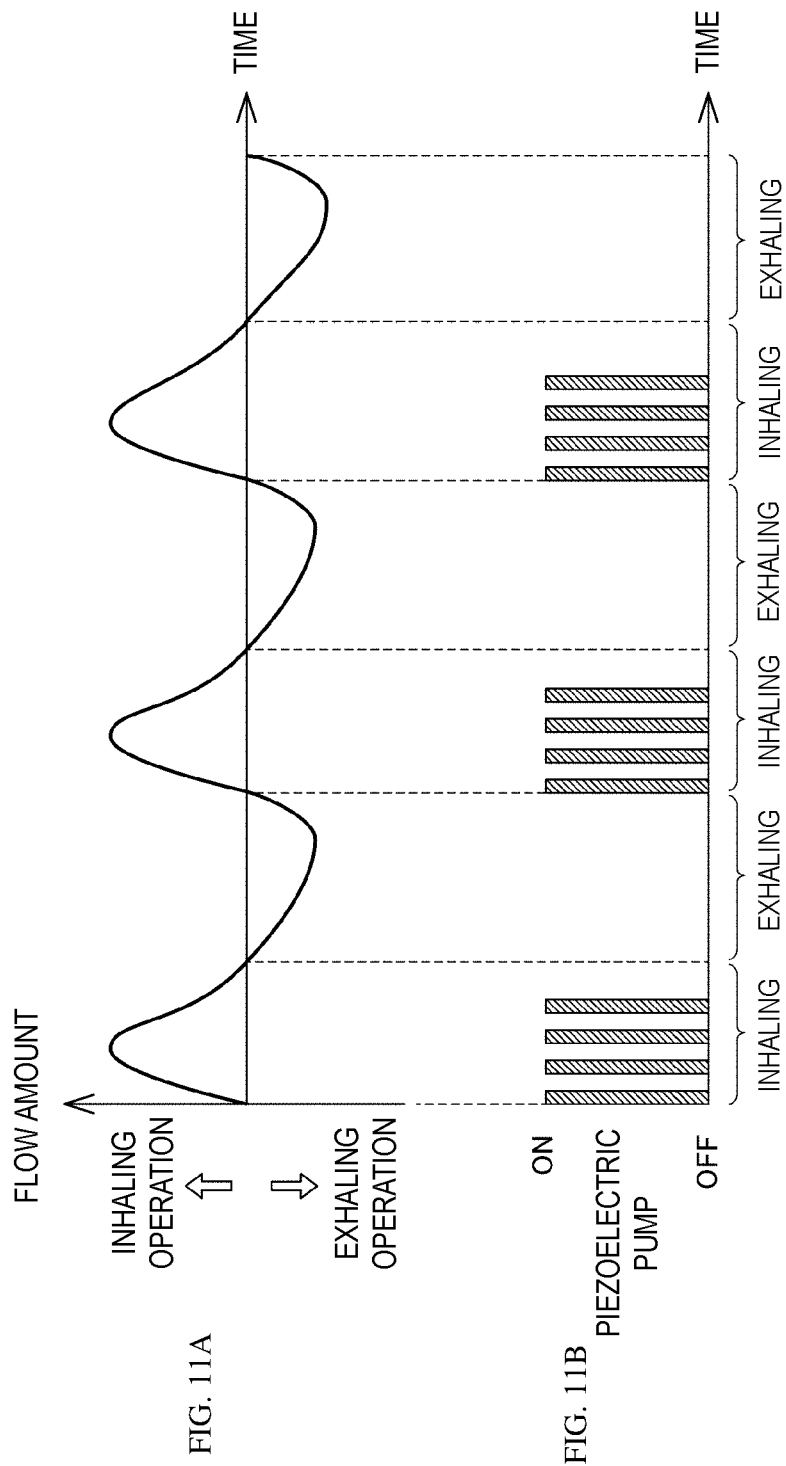

FIG. 10 is a flowchart illustrating operation of the controller of the CPAP device according to the present embodiment in the first use state. Each of FIGS. 11A and 11B is a timing chart for description of the humidification operation of the CPAP device according to the present embodiment. Next, with reference to FIGS. 10 and 11, the humidification operation in the CPAP device 1A according to the present embodiment will be described in detail.

The above-described vaporization operation performed in the CPAP device 1A according to the present embodiment is such operation that the amount of water vapor (that is, a humidification amount) generated by a single vaporization operation is fixed. Accordingly, the CPAP device 1A according to the present embodiment is configured such that, in order to humidify the air to an appropriate humidity condition, the humidification operation with the humidification mechanism is basically realized by a plurality of times of the vaporization operation to be repeatedly performed when the piezoelectric pump 260 is driven in an intermittent manner as has been described.

In order to realize the humidification operation, the CPAP device 1A according to the present embodiment is configured such that the controller 130 operates in accordance with a flow illustrated in FIG. 10 so as to allow realization of the humidification operation illustrated in FIGS. 11A and 11B.

Referring to FIG. 10, when the user operates the operation unit 131 of the CPAP device 1A to start the use, first, the controller 130 gives a drive command to the blower 140 in step S1. As a result, the blower 140 is driven and set in an ON state.

Next, in step S2, the controller 130 gives a drive command to the heater 250. As a result, the heater 250 is driven and set in an ON state, so that the temperature of the heater 250 starts to increase.

Next, in step S3, the controller 130 obtains the temperature of the heater 250. Specifically, the controller 130 obtains the temperature detected by the temperature sensor 251 attached to the heater 250.

Next, in step S4, the controller 130 determines whether the temperature of the heater 250 is lower than a set temperature having been set in advance. When the controller 130 determines that the temperature of the heater 250 is lower than the set temperature (YES in step S4), the controller 130 moves to the step S2 to continue the drive of the heater 250. In contrast, when the controller 130 determines that the temperature of the heater 250 is not lower than the set temperature (NO in step S4), the controller 130 moves to step S5. Although the set temperature of the heater 250 is not particularly limited to this, for instantaneously heating and vaporizing the water 500 supplied to the heater 250, the set temperature is preferably set to be 60° C. or higher and more preferably set to be 80° C. or higher.

In step S5, the controller 130 gives a drive stop command to the heater 250. As a result, the heater 250 stops driving and is set in an OFF state.

Next, the controller 130 obtains the temperature and humidity of humidification target air in step S6. Specifically, the controller 130 obtains the temperature and humidity of the humidification target air detected by the temperature and humidity sensor 132 provided in the upstream flow passage portion 120A of the first flow passage 120.

Next, the controller 130 obtains the flow amount and pressure of the humidification target air in step S7. Specifically, the controller 130 obtains the flow amount and pressure of the humidification target air detected by the flow amount sensor 133 and the pressure sensor 134 provided in the downstream flow passage portion 120B of the first flow passage 120.

Next, the controller 130 determines a target number of times of performing the vaporization operation in step S8. For this determination, the above-described temperature and humidity of the humidification target air detected by the temperature and humidity sensor 132 and the above-described flow amount and pressure (particularly the flow amount) of the humidification target air detected by the flow amount sensor 133 and the pressure sensor 134 are used. For example, the above-described ROM stores a data table in which the correlations between the temperature, humidity, flow amount, and pressure of the humidification target air and a corresponding optimum number of times of performing the vaporization operation are determined in advance, and the controller 130 refers to the data table to determine the target number of times of performing the vaporization operation. As the target number of times of performing the vaporization operation, the number of times of performing the vaporization operation is determined in advance from among once or a plurality of number of times in accordance with the temperature, humidity, flow amount, pressure of the humidification target air so as to obtain a humidification amount close to a normal humidification amount with which the humidification target air is to be humidified.

Next, the controller 130 determines whether the user is performing inhaling operation in step S9. For this determination, the above-described flow amount and pressure detected by the flow amount sensor 133 and the pressure sensor 134 are used. When the controller 130 determines that the user is not performing the inhaling operation (that is, the user is performing exhaling operation, NO in step S9), the controller 130 resets the target number of times of performing the vaporization operation in step S9', and then moves to step S3 to return to the obtaining of the temperature of the heater 250 again. When the controller 130 determines that the user is performing the inhaling operation (YES in step S9), the controller 130 moves to step S10.

In step S10, the controller 130 gives a drive command to the piezoelectric pump 260 for the drive for a certain period of time. As a result, for a certain period of time, the piezoelectric pump 260 continues to be in an ON state in which the piezoelectric pump 260 is driven, and the outside air 600 is introduced into the water supply passage 230. This certain period of time is a period of time required to supply all the water 500 with which the portion of the water supply passage 230 between the intermediate position 233 and the water discharge port 232 is filled to the heater 250 through the water discharge port 232. Due to the drive of the piezoelectric pump 260 for the certain period of time, a single vaporization operation is completed.

Next, the controller 130 determines whether the target number of times of performing the vaporization operation has been reached in step S11. When the controller 130 determines that the target number of times of performing the vaporization operation has not been reached (NO in step S11), the controller 130 waits for a certain period of time in step S11'. After that, in step S11', the controller 130 obtains the flow amount and pressure of the humidification target air as with step S7 described above and then moves to Step S9 to return to the determination of whether the user is performing the inhaling operation. The waiting for a certain period of time in step S11' is a period of time longer than or equal to a period of time required to fill the water supply passage 230 with the water 500 by using capillarity. When the controller 130 determines that the target number of times of performing the vaporization operation has been reached (YES in step S11), the controller 130 moves to step S12.

In step S12, the controller 130 determines whether a stop command for the CPAP device 1A has been given. Specifically, this determination is made based on whether the stop command for the use has been inputted through operation of the operation unit 131 of the CPAP device 1A by the user. When the controller 130 determines that the stop command for the CPAP device 1A has not been given (NO in step S12), the controller 130 moves to step S3 to return to the obtaining of the temperature of the heater 250 again. When the controller 130 determines that the stop command for the CPAP device 1A has been given (YES in step S12), the controller 130 moves to step S13.

In step S13, the controller 130 gives a drive stop command to the blower 140. This causes the drive of the blower 140 to stop and sets the blower 140 in the OFF state. Thus, the entirety of the operation of the CPAP device 1A have been completed.

When the controller 130 operates in accordance with the above-described serial control flow, the piezoelectric pump 260 is driven in an intermittent manner by the controller 130 so that the filling of the water supply passage 230 with the water 500 and the introduction of the outside air 600 to the intermediate position 233 of the water supply passage 230 are repeated alternately in terms of time. Accordingly, the humidification operation as illustrated in FIGS. 11A and 11B is realized.

That is, as illustrated in FIG. 11A, when the user breathes, the inhaling operation and the exhaling operation are alternately repeatedly performed. In accordance with this, the flow amount of the air in the first flow passage 120 changes. When this change in the flow amount of the air is detected by the flow amount sensor 133, the controller 130 determines whether the user is performing the inhaling operation or the exhaling operation.

As illustrated in FIG. 11B, when the controller 130 determines that the user is performing the inhaling operation, basically, the vaporization operation is performed once or a plurality of times (the drawing illustrates the case where the vaporization operation is performed four times), thereby the humidification target air can be humidified with an optimum humidification amount. It is configured such that the vaporization operation performed once or a plurality of times is completed while the user is performing the inhaling operation. Thus, while the user is performing the exhaling operation, the vaporization operation is not performed.

Accordingly, when the humidification operation is performed in accordance with the above-described control flow, the following situation can be prevented: the water vapor added to the air in the second flow passage 220 reaches the first flow passage 120 due to backflow of the water vapor caused by exhaling of the user. This can suppress failure of various components accommodated in the first housing 110 (representatively, the blower 140) due to adhering of moisture to the components or propagation of germs due to adhering of moisture to inner walls of the first housing 110. Accordingly, the CPAP device that is hygienically good and features good maintainability for cleaning can be obtained.

As has been described above, when the CPAP device 1A according to the present embodiment is used, the CPAP device which has a small size and with which humidification can be efficiently performed can be obtained. Here, the reason why the device can be configured as a size-reduced device is that the above-described humidification mechanism (particularly, the heater 250 serving as the vaporizer) can be configured such that the size of humidification mechanism can be sufficiently reduced. The reasons why the humidification can be efficiently performed are that the amount of the water 500 vaporized in a single vaporization operation is very small (for example, several µL or less) and that the total amount of energy (that is, the sum of power consumption of the heater 250 and power consumption of the piezoelectric pump 260) required to vaporize the water 500 can be suppressed because the vaporization operation is performed only at the required timing.

Another reason why the humidification can be efficiently performed is that loss of energy can be significantly reduced. In the case of a method in which all the water stored in a tank is heated being the related-art method, the amount of the heat emitted from the tank to the outside non-negligibly increases compared to the amount of the heat required to vaporize the water. Consequently, a larger amount of energy is required in total. In contrast, with the humidification mechanism according to the present embodiment, such waste of energy can be suppressed. Consequently, efficient humidification can be performed.

Furthermore, when the above-described CPAP device 1A according to the present embodiment is used, an effect can be obtained by which, even in the case where the user mistakenly causes the device to topple over, penetration of the water 500 stored in the tank chamber 216 into the blowing unit 100 or the air tube 300 through the second flow passage 220 can be prevented. The reason for this is that the water 500 does not leak to the second flow passage 220 due to the surface tension of the water 500 in a portion of the water supply passage 230 positioned at the water discharge port 232 where the water supply passage 230 communicates with the second flow passage 220. This can prevent the above-described failure of the components and flowing of the water 500 in a liquid state into the airway of the user.

From the viewpoint of preventing such unintentional leakage of the water 500 from the water discharge port 232, it is more preferable to provide either or both of a check valve and water repellent treatment described below: the check valve is provided in the water discharge port 232 and allows a movement of fluid (including the water 500 and the outside air 600) from the water supply passage 230 toward the heater 250 and limits a movement of the fluid (including the water 500 and the air passing through the second flow passage 220) from the heater 250 toward the water supply passage 230; and the water repellent treatment is provided on a flow passage forming surface of the water supply passage 230 that defines the water discharge port 232 and/or an end surface of the water discharge port 232. Such structure or structures can not only suppress the above-described leakage of the water 500 due to toppling of the CPAP device 1A but also effectively suppress the leakage of the water 500 during the filling of the water supply passage 230 with the water 500 by using capillarity in the vaporization operation. Thus, a refined humidification amount can be more reliably controlled. When the water repellent treatment is provided near the water discharge port 232, the water repellent treatment can be provided on the above-described flow passage forming surface and/or the above-described end surface of the other end portion of the water supply passage 230 where the water discharge port 232 is provided. In this case, the water repellent treatment may be provided only on part of the flow passage forming surface or only on part of the end surface.

Furthermore, when the above-described CPAP device 1A according to the present embodiment is used, an effect can be also obtained in terms of the cost. The reason for this is that the above-described humidification mechanism has a very simple structure, and the components such as the heater 250 and the piezoelectric pump 260 required to make the humidification mechanism are comparatively inexpensive. Thus, the CPAP device can be provided at a low price.

In addition, when the above-described CPAP device 1A according to the present embodiment is used, a secondary effect by which humidified air can be fed to the airway of the user shortly after the start of the use can be obtained. The reason for this is that, since the size of the heater 250 can be significantly reduced as described above, the temperature of the heater 250 can be more quickly increased to the set temperature, and accordingly, the humidification operation can be performed substantially without delay from the start of the use.

Second Embodiment

FIG. 12 is a schematic sectional view of a CPAP device according to a second embodiment of the present disclosure in the first use state. Hereafter, a CPAP device 1B according to the present embodiment will be described with reference to FIG. 12.

As illustrated in FIG. 12, compared to the above-described CPAP device 1A according to the first embodiment, the configuration of the CPAP device 1B according to the present embodiment is different from that of the CPAP device 1A mainly because the CPAP device 1B includes a differently configured humidification unit 200B. Here, the above-described humidification unit 200A according to the first embodiment is configured such that the water supply passage 230 is filled with the water 500 stored in the tank chamber 216 by using the capillarity. The humidification unit 200B according to the present embodiment is configured such that the water supply passage 230 can be filled by utilizing the capillarity or a water head difference.

The humidification unit 200B does not include a projection that projects upward in one of the four corners of the upper surface of the second housing 210. Instead, the humidification unit 200B includes a projection that projects downward in one of the four corners of the lower surface of the second housing 210. One of side surfaces of the projection provided on the lower surface of the second housing 210 is included in the tube connection surface 211 to which the air tube 300 is connected in the first use state. Another of the side surfaces of the above-described projection is included in the second connection surface 213 to be connected to the blowing unit 100 in the first use state.

Part of the lower surface of the second housing 210 except for the above-described projection is included in a placement surface 219 to be placed on the blowing unit 100 in the first use state. In addition, the upper surface of the first housing 110 of the blowing unit 100 is included in a placement surface 118 on which the humidification unit 200B is to be placed in the first use. The lower surface of the first housing 110 is included in a placement surface to be placed on a floor, a table, or the like in the first use state.

That is, the CPAP device 1B according to the present embodiment is configured such that the humidification unit 200B can be attached to the blowing unit 100 when the humidification unit 200B is placed on the blowing unit 100. The operation surface in which the operation unit of the blowing unit 100 is provided is configured with one of the four side surfaces of the first housing 110 except for the first connection surface 113.

The space inside the second housing 210 is separated into the tank chamber 216 and the vaporization chamber 217 by the partition 215. Out of these, the vaporization chamber 217 is provided so as to include as part thereof the above-described projection provided on the lower surface of the second housing 210. The water supply passage 230 is disposed in the vaporization chamber 217. The heater 250 is installed in a lower portion of a space inside the above-described projection. The vaporization chamber 217 corresponds to the second flow passage 220 that connects the second inlet 221 and the second outlet 222 to each other.

The water supply passage 230 includes a pipe bent into a substantially L shape. The one end portion of the water supply passage 230 penetrates through the partition 215 and is connected to the tank chamber 216. Meanwhile, the other end portion of the water supply passage 230 is disposed above the heater 250 so as to face the heater 250. In this way, the water supply passage 230 is made to connect the tank chamber 216 serving as the reservoir and the heater 250 serving as the vaporizer to each other.

The above-described one end portion of the water supply passage 230 corresponds to the water supply port 231 that allows the water 500 stored in the tank chamber 216 to be supplied toward the water supply passage 230 therethrough. The above-described other end portion of the water supply passage 230 corresponds to the water discharge port 232 that allows the water 500 having been supplied to the water supply passage 230 through the water supply port 231 to be discharged toward the heater 250 therethrough. Here, the water supply port 231 is disposed above the water discharge port 232, thereby the water 500 stored in the tank chamber 216 flows into the water supply passage 230 due to the capillarity or the water head difference. Consequently, the water supply passage 230 is normally maintained in a state in which the water supply passage 230 is filled with the water 500.

Here, when the capillarity is utilized, it is sufficient that the inner diameter of the above-described pipe included in the water supply passage 230 be set to, for example, greater than or equal to 0.1 mm and smaller than or equal to 1.0 mm. In this case, even without adding particular contrivance to the water discharge port 232, the water 500 having flowed into the water supply passage 230 stops at the water discharge port 232 due to the surface tension thereof. Thus, normally, the water 500 is not supplied to the heater 250.

In contrast, when the water head difference is utilized, the inner diameter of the above-described pipe included in the water supply passage 230 can be increased compared to the case of utilizing the capillarity. However, in order to stop the water 500 having flowed into the water supply passage 230 at the water discharge port 232 (that is, normally, to prevent the water 500 from being supplied to the heater 250), it is required to make predetermined contrivance at the water discharge port 232. The details of the contrivance will be described later.

The outside-air introduction passage 240 that can introduce the outside air 600 therethrough is connected to an intermediate position of the water supply passage 230. Here, all of the outside-air introduction passage 240, the check valve 241 that serves as the penetration preventer and is installed in the outside-air introduction passage 240, and the piezoelectric pump 260 connected to the outside-air introduction passage 240 are similar to those in the above-described first embodiment. Thus, the description of those components is not repeated.

Also, in the case where the CPAP device 1B having the above-described configuration is used, as with the case where the CPAP device 1A according to the first embodiment is used, the piezoelectric pump 260 is driven in an intermittent manner by the controller 130 so that the filling of the water supply passage 230 with the water 500 and the introduction of the outside air 600 to the intermediate position 233 of the water supply passage 230 are repeated alternately in terms of time. Thus, the performing of the vaporization operation and the realization of the humidification operation having been described are possible. Accordingly, also when the present configuration is adopted, effects similar to the effects described in the above-described first embodiment can be obtained.

FIGS. 13A to 13D include schematic sectional views of specific examples of the structure of the water discharge port of the water supply passage illustrated in FIG. 12. Next, with reference to FIGS. 13A to 13D, some specific examples of the above-described contrivance are described which are made for normally stopping the water 500 having flowed into the water supply passage 230 at the water discharge port 232 in the case where the water head difference is utilized in the CPAP device 1B according to the present embodiment.

Figure 13A:
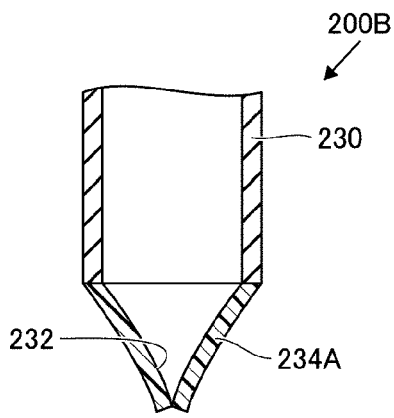

In a specific example illustrated in FIG. 13A, a check valve 234A is provided at the above-described other end portion of the water supply passage 230. The check valve 234A is formed of, for example, an elastic body, and the water discharge port 232 of the water supply passage 230 is defined by this check valve 234A. In this case, normally, the check valve 234A does not allow the movement of the fluid (including the water 500 and the outside air 600) from the water supply passage 230 toward the heater 250. Meanwhile, when the outside air 600 is introduced into the water supply passage 230, the pressure of the outside air 600 opens the check valve 234A. Thus, the movement of the fluid from the water supply passage 230 to the heater 250 are allowed until this pressure is eliminated.

Figure 13B:
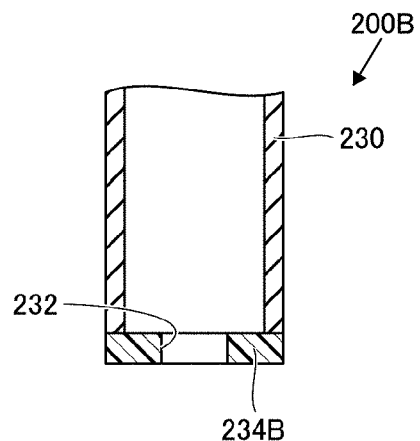
Figure 13C:
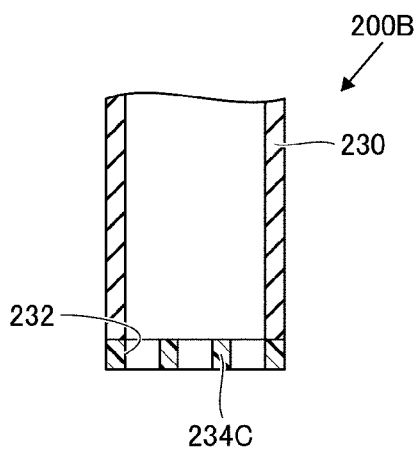
Figure 13D:
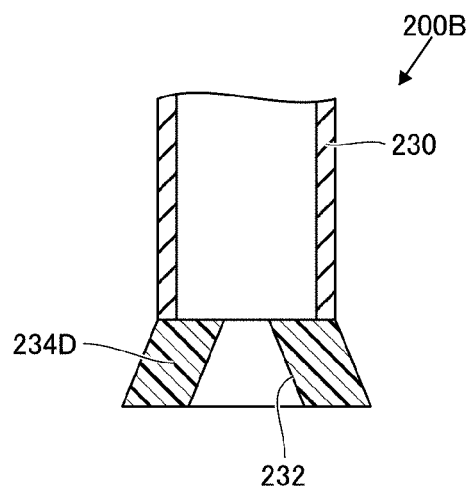

In specific examples illustrated in FIG. 13B to FIG. 13D, nozzles 234B to 234D are provided at the above-described other end portion of the water supply passage 230. Here, the nozzles 234B to 234D are configured such that each of the nozzles 234B to 234D has the water discharge port 232 that is smaller than the inner diameter of the water supply passage 230, thereby increasing the surface tension generated in a portion of the water 500 in contact with the water discharge port 232. In this way, normally, the movement of the fluid (including the water 500 and the outside air 600) from the water supply passage 230 toward the heater 250 are not allowed, and when the outside air 600 is introduced into the water supply passage 230, the pressure of the outside air 600 pushes out the fluid from the water supply passage 230 to the heater 250.

Here, the nozzle 234B having a shape illustrated in FIG. 13B is configured such that the water discharge port 232 is defined by a single hole. The nozzle 234C having a shape illustrated in FIG. 13C is configured such that the water discharge port 232 is defined by a plurality of holes. The nozzle 234D having a shape illustrated in FIG. 13D is configured such that the water discharge port 232 is defined by a single hole the sectional area of which downwardly increases. With the nozzle 234C having the shape illustrated in FIG. 13C, the water 500 is supplied to the heater 250 as with the case where a shower is used, and with the nozzle 234D having the shape illustrated in FIG. 13D, the water 500 is supplied to a larger region of the heater 250. Thus, with the nozzle 234C or 234D, an effect by which vaporization of the water 500 with the heater 250 is facilitated more than with the nozzle 234B having the shape illustrated in FIG. 13B can be obtained.

Each of the above-described check valve 234A illustrated in FIG. 13A and the above-described nozzles 234B to 234D illustrated in FIG. 13B to FIG. 13D may be formed of a water repellent material. In this case, the water 500 is repelled from the water discharge port 232 defined by the check valve 234A or one of the nozzles 234B to 234D. Thus, such a configuration is possible in which, normally, the movement of the fluid (including the water 500 and the outside air 600) from the water supply passage 230 toward the heater 250 are not allowed, and, when the outside air 600 is introduced into the water supply passage 230, the pressure of the outside air 600 pushes out the fluid from the water supply passage 230 to the heater 250.

Third Embodiment

FIG. 14 illustrates the configuration of functional blocks of the CPAP device according to a third embodiment of the present disclosure in the first use state. FIG. 15 is a schematic sectional view of the CPAP device in the first use state. Next, with reference to FIGS. 14 and 15, the configuration and a detailed structure of the functional blocks of a CPAP device 1C according to the present embodiment in the first use state are described.

As illustrated in FIGS. 14 and 15, compared to the above-described CPAP device 1A according to the first embodiment, the configuration of the CPAP device 1C according to the present embodiment is different from that of the CPAP device 1A mainly because the CPAP device 1C includes a differently configured humidification unit 200C. Here, the above-described humidification unit 200A according to the first embodiment is configured such that the water 500 is supplied to the heater 250 serving as the vaporizer by using the piezoelectric pump 260 or the like serving as the gas introduction source. The humidification unit 200C according to the present embodiment is configured such that the water 500 can be supplied to the heater 250 by using a spot heater 270 serving as a heating source instead of the piezoelectric pump 260 or the like.

In the CPAP device 1C, the above-described spot heater 270 is installed in the vaporization chamber 217 provided in the second housing 210 of the humidification unit 200C. In more detail, the spot heater 270 has, for example, an annular shape and is provided in the water supply passage 230 so as to surround the intermediate position of the water supply passage 230. The spot heater 270 is driven by the controller 130 and can locally heat the water supply passage 230, thereby the water 500 positioned near a portion where the spot heater 270 is provided is instantaneously heated and evaporated. Thus, water vapor 502 is generated in the water supply passage 230.

FIGS. 16A to 16D include schematic views for description of vaporization operation in the CPAP device according to the present embodiment. Next, with reference to FIGS. 16A to 16D, the vaporization operation in the CPAP device 1C according to the present embodiment will be described in detail. FIGS. 16A to 16D sequentially illustrate a single vaporization operation, and the vaporization operation proceeds in the order of FIG. 16A to FIG. 16B.

Figure 16A:
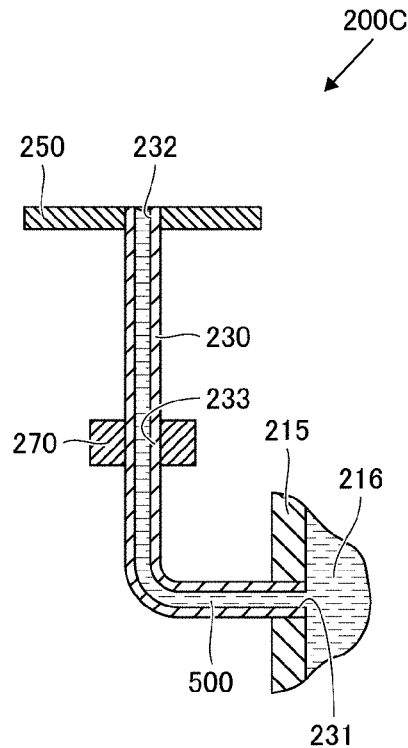

First, as illustrated in FIG. 16A, before the start of the vaporization operation, the water 500 stored in the tank chamber 216 flows into the water supply passage 230 through the water supply port 231 in accordance with the capillarity. Thus, the water supply passage 230 is filled with the water 500 having flowed thereinto. At this time, the water 500 having flowed into the water supply passage 230 stops at the water discharge port 232 due to the surface tension thereof. Thus, the water 500 is not supplied to the heater 250.

Figure 16B:
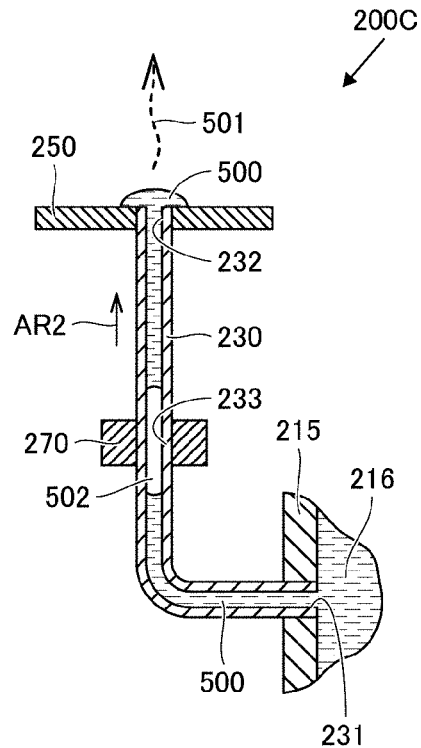

Next, as illustrated in FIG. 16B, the spot heater 270 is driven so as to start the vaporization operation. Consequently, the water vapor 502 is generated at the intermediate position 233 of the water supply passage 230 where the spot heater 270 is provided. When the water vapor 502 is generated, the water 500 with which a portion of the water supply passage 230 between the intermediate position 233 and the water discharge port 232 is filled receives the pressure of the water vapor 502 so as to be moved in an arrow AR2 direction in the drawing. Thus, the water 500 is pushed out through the water discharge port 232, thereby supplying of the water 500 to the heater 250 is started. The water supplied to the heater 250 is instantaneously heated by the heater 250 and vaporized so as to become the water vapor 501 and added to the air passing through the second flow passage 220.

Figure 16C:
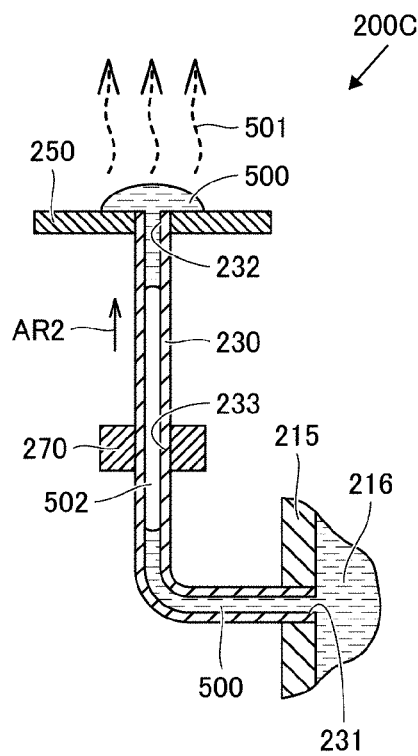

Subsequently, as illustrated in FIG. 16C, a more amount of the water vapor 502 is generated in the water supply passage 230 due to the drive of the spot heater 270. Thus, the water 500 is sequentially pushed out so as to be supplied to the heater 250, and accordingly, generation of the water vapor 501 continues. At this time, the water vapor 502 having been generated in the water supply passage 230 is also gradually moved to the water discharge port 232 side in the arrow AR2 direction in the drawing.

Figure 16D:
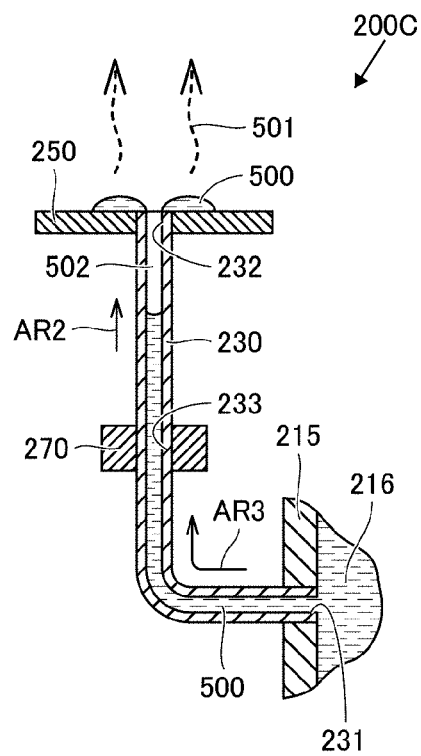

Next, as illustrated in FIG. 16D, after a certain period of time has elapsed from the start of the drive of the spot heater 270, the drive of the spot heater 270 is stopped. This causes the generation of the water vapor 502 at the intermediate position 233 to stop, and, due to the capillarity, the water 500 flows again from the tank chamber 216 into the water supply passage 230 through the water supply port 231 in an arrow AR3 direction in the drawing. At this time, all the water vapor 502 having been generated at the intermediate position 233 of the water supply passage 230 is pushed out through the water discharge port 232 by the water 500 having flowed into the water supply passage 230. Along with this, all the water 500 with which the portion of the water supply passage 230 between the intermediate position 233 and the water discharge port 232 has been filled at the start of the vaporization operation is also pushed out through the water discharge port 232 and vaporized by the heater 250.

When the above-described process has been performed, a single vaporization operation is completed. In order to vaporize all the water 500 with which, as described above, the portion of the water supply passage 230 between the intermediate position 233 and the water discharge port 232 is filled at the start of the vaporization operation, it is sufficient that the water vapor 502 having a volume larger than or equal to the volume of this portion of the water supply passage 230 be generated in the water supply passage 230 with the spot heater 270.

FIG. 17 is a flowchart illustrating the operation of the controller of the CPAP device according to the present embodiment in the first use state. Each of FIGS. 18A and 18B is a timing chart for description of the humidification operation of the CPAP device according to the present embodiment. Next, with reference to FIGS. 17, 18A and 18B, the humidification operation in the CPAP device 1C according to the present embodiment will be described in detail.

The above-described vaporization operation performed in the CPAP device 1C according to the present embodiment is such operation that the amount of water vapor (that is, a humidification amount) generated by a single vaporization operation is fixed. Accordingly, the CPAP device 1C according to the present embodiment is configured such that, in order to humidify the air to an appropriate humidity condition, the humidification operation with the humidification mechanism is basically realized by a plurality of times of the vaporization operation to be repeatedly performed when the spot heater 270 is driven in an intermittent manner.

In order to realize the humidification operation, the CPAP device 1C according to the present embodiment is configured such that the controller 130 operates in accordance with a flow illustrated in FIG. 17 so as to allow realization of the humidification operation illustrated in FIGS. 18A and 18B.

Here, as illustrated in FIG. 17, a control flow of the controller 130 in the CPAP device 1C according to the present embodiment follows the control flow illustrated in FIG. 10. Only the difference is that, according to the control flow illustrated in FIG. 17, a single vaporization operation in step S10 is realized when the controller 130 gives a drive command for the drive of the spot heater 270 for a certain period of time.

When the controller 130 operates in accordance with the serial control flow illustrated in FIG. 17, the spot heater 270 is driven in an intermittent manner by the controller 130 so that the filling of the water supply passage 230 with the water 500 and the generation of the water vapor 502 at the intermediate position 233 of the water supply passage 230 are repeated alternately in terms of time. Accordingly, the humidification operation as illustrated in FIGS. 18A and 18B is realized.

Accordingly, also when the CPAP device 1C having the above-described configuration is used, effects similar to the effects described in the above-described first embodiment can be obtained. Thus, the CPAP device which has a small size and with which humidification can be efficiently performed can be obtained.

(Other Forms and So Forth)

In the above-described first to third embodiments, the description is made by exemplifying the case where the present disclosure is applied to the CPAP device serving as the respiratory humidification and blowing apparatus. However, the present disclosure can be applied to any of a steam inhaler, an oxygen inhaler, and the like in addition to the CPAP device. The present disclosure can be applied to any application as long as the application is an apparatus that includes a humidification device, and, of course, the present disclosure can also be applied to any of apparatuses other than the respiratory humidification and blowing apparatus. Furthermore, in the case where the humidification device is used standalone, the present disclosure can also be effectively applied.

In the above-described first to third embodiments, the description is made by exemplifying the case where the heater that heats the water is used as the vaporizer. However, the vaporizer is not necessarily configured as described above. Anything that is capable of evaporating water can be used as the vaporizer. When an atomizer (for example, an ultrasonic vibrator or the like) is provided instead of the vaporizer, this can be utilized as an atomization device. Examples of such an atomization device include, for example, a nebulizer as a respiratory atomization device.

In the above-described first and second embodiments, the description is made by exemplifying the case where the piezoelectric pump is used as the gas introduction source. However, the gas introduction source does not necessary include the piezoelectric pump. Anything that is capable of pumping gas can be used as the gas introduction source. In this case, the gas introduction source is not limited to a source for introduction of the outside air into a water supply part. When, for example, a tank filled with compressed gas is used, gas other than the outside air can be introduced to the water supply part.

In the above-described first and second embodiments, the description is made by exemplifying the case of the configuration in which the air is introduced into the water supply passage. However, the gas introduced into the water supply passage is not limited to the air. For example, in the case of the above-described oxygen inhaler, it is preferable that oxygen be introduced into the water supply passage.

Furthermore, the characteristic configurations disclosed in the above-described first to third embodiments can be combined with each other without departing from the gist of the present disclosure.

As has been described, the above-described embodiments disclosed herein are exemplary in all respects and are not limiting. The technical scope of the present disclosure is defined by the scope of claims and embraces all the modifications within meaning and the scope equivalent to the description in the scope of claims.

1A to 1C CPAP device
100 blowing unit
110 first housing
111 operation surface
112 placement surface
113 first connection surface
114 separation wall
115 wide portion
116 narrow portion
117 blower chamber 118 placement surface
120 first flow passage
120A upstream flow passage portion
120B downstream flow passage portion
121 first inlet
122 first outlet
130 controller
131 operation unit
132 temperature and humidity sensor
133 flow amount sensor
134 pressure sensor
140 blower
141 impeller
142 casing
143 suction port
144 discharge port
150 silencer
160 hose
170 filter
171 filter cover
200A to 200C humidification unit
210 second housing
211 tube connection surface
212 placement surface
212a cavity
213 second connection surface
214 lid
215 partition
216 tank chamber
217 vaporization chamber
218 outside-air intake
219 placement surface
220 second flow passage
221 second inlet
222 second outlet
230 water supply passage
231 water supply port
232 water discharge port
233 intermediate position
234A check valve
234B to 234D nozzle
240 outside-air introduction passage
241 check valve
250 heater
251 temperature sensor
260 piezoelectric pump
270 spot heater
300 air tube
400 mask
500 water
501, 502 water vapor
600 outside air
601 bubble.

The invention claimed is:

1. A humidification device comprising:
a reservoir for storing water;
a vaporizer for vaporizing the water supplied to the vaporizer;
a water supply passage connected to the reservoir at one end portion, and connected to the vaporizer at another end portion, wherein the water supply passage is filled with the water flowing into the water supply passage when the water stored in the reservoir flows into the water supply passage through the one end portion;
a gas introduction passage connected to an intermediate position of the water supply passage;
a gas introduction source for introducing gas into the water supply passage through the gas introduction passage so as to push out, by using pressure of the introduced gas, toward the vaporizer the water filled in a portion of the water supply passage between the intermediate position and the other end portion, thereby supplying the water to the vaporizer;
a housing, wherein the reservoir, the vaporizer, the water supply passage, and the gas introduction passage are all disposed within said housing, wherein said housing has a placement surface configured to receive a blowing device thereon, wherein a projection projects outwards from said placement surface, and wherein a flow passage is defined within said projection, said flow passage directly receiving the vaporized water from said vaporizer;
a lid provided at said placement surface and configured to provide selective access to said reservoir;
a penetration preventer for preventing penetration of the water from the water supply passage to the gas introduction source, said penetration preventer being provided in the gas introduction passage; and
a controller for controlling an operation of the gas introduction source, wherein
the controller drives the gas introduction source in an intermittent manner such that filling of the water supply passage with the water and introduction of the gas to the intermediate position are repeated alternately in terms of time.

2. The humidification device according to claim 1, wherein the gas introduction source includes a piezoelectric pump.

3. The humidification device according to claim 2, wherein the gas introduction source introduces air to the water supply passage.

4. The humidification device according to claim 2, wherein the water supply passage is filled with the water by utilizing capillarity.

5. The humidification device according to claim 2, wherein a check valve for allowing a movement of a fluid from the water supply passage toward the vaporizer and limiting the movement of the fluid from the vaporizer toward the water supply passage is provided at the other end portion.

6. The humidification device according to claim 1, wherein the gas introduction source introduces air to the water supply passage.

7. The humidification device according to claim 6, wherein the water supply passage is filled with the water by utilizing capillarity.

8. The humidification device according to claim 1, wherein the water supply passage is filled with the water by utilizing capillarity.

9. The humidification device according to claim 1, wherein a check valve for allowing a movement of a fluid from the water supply passage toward the vaporizer and limiting the movement of the fluid from the vaporizer toward the water supply passage is provided at the other end portion.

10. The humidification device according to claim 1, wherein water repellent treatment is provided on one or both of a flow passage forming surface of the other end portion and an end surface of the other end portion.

11. The humidification device according to claim 1, wherein the vaporizer includes a heater for heating the water supplied to the heater.

12. A respiratory humidification and blowing apparatus, the apparatus comprising:
the humidification device according to claim 1, wherein:
the blowing device includes a blower for feeding gas to an airway of a user, and
a gas current generated by driving the blower is humidified by the humidification device.

13. The respiratory humidification and blowing apparatus according to claim 12, the apparatus further comprising:
a respiratory state detector for detecting a respiratory state of the user, wherein
the controller determines whether the user performs inhaling operation or exhaling operation in accordance with a result of detection performed by the respiratory state detector, and wherein,
in a case where the controller determines that the user performs the inhaling operation, humidification operation with the humidification device is performed, and in a case where the controller determines that the user performs the exhaling operation, the humidification operation with the humidification device is stopped.

14. The respiratory humidification and blowing apparatus according to claim 13, wherein the vaporizer is configured to perform a vaporization operation once or a plurality of times during a period of time after a time at which the controller determines that the user performs the inhaling operation to a time at which the controller determines that the user performs the exhaling operation.

15. The humidification device according to claim 1, wherein an outlet is provided on a first surface of the projection, said outlet being in fluid communication with said flow passage.

16. The humidification device according to claim 15, wherein an inlet is provided on a second surface of the projection, said inlet being configured to receive air from outside said housing, and wherein said first and second surfaces of the projection are facing opposite, respective directions.

* * * * *